United States Patent
Hetting

(10) Patent No.: US 11,660,398 B2
(45) Date of Patent: May 30, 2023

(54) STOPPER WITH LOW FORCE FOR USE IN AN INJECTOR

(71) Applicant: INJECTO GROUP A/S, Hellerup (DK)

(72) Inventor: Mikael Hetting, Charlottenlund (DK)

(73) Assignee: INJECTO GROUP A/S, Hellerup (DK)

( * ) Notice: Subject to any disclaimer, the term of this patent is extended or adjusted under 35 U.S.C. 154(b) by 0 days.

(21) Appl. No.: 17/042,070

(22) PCT Filed: Mar. 27, 2019

(86) PCT No.: PCT/DK2019/050105
§ 371 (c)(1),
(2) Date: Sep. 25, 2020

(87) PCT Pub. No.: WO2019/185101
PCT Pub. Date: Oct. 3, 2019

(65) Prior Publication Data
US 2021/0046248 A1    Feb. 18, 2021

(30) Foreign Application Priority Data

Mar. 27, 2018  (DK) ............................. PA 2018-00135
Sep. 24, 2018  (DK) ............................. PA 2018-00637

(51) Int. Cl.
    *A61M 5/315* (2006.01)
(52) U.S. Cl.
    CPC . *A61M 5/31513* (2013.01); *A61M 2205/0222* (2013.01)
(58) Field of Classification Search
    CPC ...... A61M 5/31513; A61M 2205/0222; A61M 5/3129; A61M 5/31515; A61M 5/1454;
    (Continued)

(56) References Cited

U.S. PATENT DOCUMENTS

| | | |
|---|---|---|
| 8,475,415 B2 | 7/2013 | Schiller et al. |
| 2007/0219508 A1* | 9/2007 | Bisegna ............ A61M 5/31513 604/218 |

(Continued)

FOREIGN PATENT DOCUMENTS

| | | | |
|---|---|---|---|
| EP | 1849490 A1 * | 10/2007 | ........ A61M 5/31515 |
| EP | 1849490 A1 | 10/2007 | |

(Continued)

OTHER PUBLICATIONS

Evoprene™ G Thermoplastic Elastomer (TPE) Compounds, AlphaGary, Jul. 2007, 2 pages.

(Continued)

*Primary Examiner* — Bhisma Mehta
*Assistant Examiner* — Nidah Hussain
(74) *Attorney, Agent, or Firm* — Holland & Hart LLP

(57) ABSTRACT

The present invention relates to a stopper for an injector for delivery of a pharmaceutical composition and to an injector with the stopper. The stopper has a stopper body with an actuating surface opposite an outlet surface, an axial length between the actuating surface and the outlet surface, and a transverse diameter, which stopper body defines an access diameter, the stopper at an axial location from the actuating surface comprising a deformable sealing element surrounding the stopper body and having an outer diameter, which is larger than the transverse diameter, which deformable sealing element is made from a thermoplastic elastomer and has an axial extension in the range of 5% and 95% of the axial length of the stopper body, and the stopper comprising a cavity at the axial location of the deformable sealing element, the cavity having a lateral extension larger than the access diameter of the stopper body.

23 Claims, 13 Drawing Sheets

(58) Field of Classification Search
CPC .......... A61M 5/31585; A61M 5/31583; A61M 2005/3131; A61M 2005/14506
USPC ........................................................ 604/222
See application file for complete search history.

(56) References Cited

U.S. PATENT DOCUMENTS

| | | | |
|---|---|---|---|
| 2011/0034882 A1* | 2/2011 | Quinn | A61M 5/31511 604/218 |
| 2012/0253291 A1 | 10/2012 | Ivosevic et al. | |
| 2015/0119817 A1* | 4/2015 | Prasad | A61M 5/31513 525/240 |
| 2016/0243311 A1 | 8/2016 | Fournier et al. | |
| 2017/0368264 A1 | 12/2017 | Fournier et al. | |
| 2018/0043102 A1* | 2/2018 | Cojocariu | A61M 5/31513 |

FOREIGN PATENT DOCUMENTS

| | | |
|---|---|---|
| EP | 2703025 A1 | 3/2014 |
| EP | 3437680 A1 | 2/2019 |
| JP | 2000107290 | 4/2000 |
| JP | 2010-528773 A | 8/2010 |
| KR | 10-2016-0068791 | 6/2016 |
| KR | 10-2017-0109593 | 9/2017 |
| WO | 20040033006 A2 | 4/2004 |
| WO | 2010/062804 A1 | 6/2010 |
| WO | 20140194918 A1 | 12/2014 |
| WO | 20160039816 A1 | 3/2016 |
| WO | 20170157396 A1 | 9/2017 |
| WO | 2019/199901 A1 | 10/2019 |
| WO | 2021/110910 A2 | 6/2021 |

OTHER PUBLICATIONS

Evoprene™ GC Thermoplastic Elastomer (TPE) Compounds, AlphaGary, Jul. 2007, 2 pages.
Evoprene™ HP Thermoplastic Elastomer (TPE) Compounds, AlphaGary, Jul. 2007, 2 pages.
Evoprene™ Super G Thermoplastic Elastomer (TPE) Compounds, AlphaGary, Jul. 2007, 2 pages.
Evoprene™ Thermoplastic Elastomer (TPE) Compounds—General Information, AlphaGary, Jul. 2007, 4 pages.
International Search Report and Written Opinion for International Application No. PCT/DK2019/050105, dated Jun. 28, 2019, 11 pages.
International Preliminary Report on Patentability for International Application No. PCT/DK2019/050105, dated Aug. 21, 2020, 10 pages.
Intellectual Property Office of India; Examination Report issued in Indian Application No. 202017045628; dated Apr. 27, 2022; 5 pages.
Chinese Patent Office, "Office Action and Search Report," issued in connection with Chinese Patent Appl. No. 201980029271.0 dated Mar. 15, 2022 (9 pages).
Korean Intellectual Property Office; Notice for Granting Patent issued in Korean Application No. 10-2020-7030007; dated Apr. 27, 2022; 5 pages.

* cited by examiner

STOPPER WITH LOW FORCE FOR USE IN AN INJECTOR

CROSS REFERENCE TO RELATED APPLICATIONS

This application is a U.S. National Entry and claims priority to PCT International Patent Application No. PCT/DK2019/050105, filed 27 Mar. 2019, and entitled "STOPPER WITH LOW FORCE FOR USE IN AN INJECTOR", which claims priority to Denmark Patent Application No. PA 2018-00135 filed 27 Mar. 2018, and Denmark Patent Application No. PA 2018-00637 filed 2018 Sep. 24, the entire disclosures of which are incorporated herein by this reference.

TECHNICAL FIELD

The present invention relates to a stopper for an injector, and to an injector having a reduced break loose force (BLF). The stopper comprises a deformable sealing element made of a thermoplastic elastomer (TPE), and the injector comprises a cylinder extending along a longitudinal axis, the cylinder having an inner wall, an outer wall, and an outlet at an outlet end opposite an actuating end. The injector of the invention provides a reduced BLF, and is especially suited for pre-filled injectors with pharmaceutical compositions allowing long term storage.

BACKGROUND

An injector for delivery of a pharmaceutical composition typically comprises a piston in a cylinder so that the piston can be pushed from one end of the cylinder to the other thereby ejecting liquid contained in the cylinder. A piston in a cylinder will abut the inner wall of the cylinder and at the interface between the piston and the inner wall there will be a static friction and a dynamic friction. Movement of the piston in the cylinder will require application of a force sufficient to overcome initially the static friction and subsequently the dynamic friction; the static friction will be larger than the dynamic friction and thereby the force to provide an initial movement of the piston is larger than the force required to provide a sustained movement of the piston. Once the piston has stopped moving the force to provide an initial movement must be overcome again. Traditionally, the inner wall of the cylinder is lubricated in order to keep the dynamic friction sufficiently low to ensure sufficient glide for the piston and allow for easy movement of the piston in the cylinder and thereby easy delivery of a pharmaceutical composition during injection. The static friction is often, in the context of pharmaceutical injectors, referred to as the "break loose force" (BLF), and the dynamic friction is commonly referred to as the "glide force". The dynamic friction may also be referred to as the "extrusion force" or "mean force". In order to provide injectors that are pleasant and easy to use there is an interest in providing injectors having low BLF values. A low BLF is especially significant for the beginning of the injection administration.

BLF depends on several factors but is especially sensitive to increased duration of the interaction between the piston's sealing element(s) and the inner wall of the syringe. Unlike traditional syringes which are filled and emptied within a few minutes prefilled syringes are shelved over longer periods of time which causes a tendency for the sealing element(s) to attach themselves to the inner wall of the syringe, which is also known as the "stick effect" and which increases over time and is further increased by ambient adverse conditions such as increased temperature, humidity, etc.

BLF is especially critical concerning prefilled syringes since these are shelved in periods of up to three years. Normally the problem concerning high BLF is solved by lubricating the piston and/or the inner wall of the syringe, but tests have shown that silicone lubrication may often have an adverse effect causing proteins in liquid injectable pharmaceutical compositions to aggregate leaving them inefficient, damaged or even harmful to the patient receiving the injection. For example, although silicone is a natural lubricant and has been successfully used for the lubrication of traditional syringes through decades there are certain drug formulations where the silicone lubricant represents a serious health threat to the patient, such as treatment of various forms of macular degeneration and diabetic macular edema, diabetic retinopathy, and myopic choroidal neovascularisation. These types of medication are anti-VEGF (anti-vascular endothelial growth factor) medications. Furthermore, these medications are administered by injection into the eye, and are delivered to the doctor in small vials and the solution must be drawn out using a syringe (unless a pre-filled syringe is used). The needle is then replaced with a smaller needle for injection into the eye. Due to the lubrication of the syringe component(s) silicone from the syringe can leach into the solution, which results in silicone droplets/particles being injected into the patient's eye. If this occurs, the silicone particles can obstruct a person's vision and severely interfere with daily life. Moreover, in connection with ophthalmic injections the silicone lubricant has a tendency to remain in the eye, which alone is undesirable.

Insulin, heparin and other drug formulations requiring subcutaneous or intra-dermal injection administration represent another large area of injection practice where the presence of silicone lubrication is a threat to the health of the patient, since it is well known that frequent injections around the same injection site on a daily basis cause scar tissue in the injection site of the patient due to the presence of silicone in each injection.

BLF is even more critical concerning glass syringes, especially prefilled syringes, since the containers of these unlike precision moulded plastic containers are manufactured with substantially higher tolerances leading to pistons which either fit too tightly or the opposite, dictating the use of lubrication. For the inner diameter of the most common glass syringes the container inner diameter may vary up to plus or minus 2/10 millimetre, depending on syringe container size, resulting in a total discrepancy of up to 0.4 mm from one container to another which has a significant influence on the friction between piston and the container inner wall and hence the BLF, and since the sealing is absolutely imperative in order to comply with the standards of container closure integrity (CCI) existing pistons for glass containers must have an outer diameter which is significantly larger than the corresponding diameter when the container diameter is on the low side.

The best pistons of the prior art commonly have BLF between 8 and 14 N and mean gliding forces of 6 to 8 N when measured in non-lubricated 1.0 ml borosilicate glass containers when tested with different liquid formulations. The indicated ranges can be attributed to the difference in container inner diameter (ID) tolerances, which may vary ±0.10 mm for glass containers.

Several suggestions exist in the prior art to address various problems relating to the general user comfort of syringes or to achieve other more specific aims.

Several manufacturers within the industry have sought to eliminate the addition of silicone lubricants and instead other solutions have been introduced with various baked-on surfaces or the like, which are supposed to reduce the force needed to initiate movement of the piston. Numerous suggestions exist in the prior art to address the problem of lowering the BLF and these typically involve modifications of the lubricant, for example, how the lubricant is applied or the type of lubricant, e.g. with respect to viscosity. As an alternative WO 2014/194918 suggests how the BLF may be controlled using special designs of the piston. A further alternative is disclosed in WO 2017/157396.

EP 2703025 discloses a gasket for a syringe, which is laminated with an inert resin film. The gasket is exemplified as a chlorinated butyl rubber gasket with a fluororesin film. The gasket is suggested to have a cavity to decrease the sliding resistance of the gasket.

It is expected that further improvements are possible and it is an aim of the present invention to provide a stopper for an injector providing a reduced BLF in the injector.

DISCLOSURE OF THE INVENTION

The present invention relates to stopper for an injector for delivery of a pharmaceutical composition, the stopper having a stopper body with an actuating surface opposite an outlet surface, an axial length between the actuating surface and the outlet surface, and a transverse diameter, which stopper body defines an access diameter, the stopper at an axial location from the actuating surface comprising a deformable sealing element surrounding the stopper body and having an outer diameter, which is larger than the transverse diameter, which deformable sealing element is made from a thermoplastic elastomer (TPE) and has an axial extension in the range of 5% and 95% of the axial length of the stopper body, and the stopper comprising a cavity at the axial location of the deformable sealing element, the cavity having a lateral extension larger than the access diameter of the stopper body.

The stopper of the invention comprises a cavity, and the location of the cavity will overlap with the location of the deformable sealing element. EP 2703025 suggests a gasket for a syringe, which gasket has a cavity formed on top of a screw located at a front circular rib of the gasket. The cavity of EP 2703025 is thought to provide a decrease in the sliding resistance of the gasket. However, the present inventor has now observed that when a cavity as suggested in EP 2703025 was included in a stopper with a deformable sealing made from a TPE the cavity provided no effect on the break loose force (BLF). The present inventor has now surprisingly found that by having a cavity at the location of the deformable sealing element according to the present invention, i.e. when there is an overlap in the axial location of the deformable sealing element and the cavity and when the diameter of the cavity was larger than the access diameter of the stopper body, the BLF for moving the stopper in an injector is reduced compared to a stopper not having the cavity. In particular, the BLF was reduced to a level where the stopper could be used without an external lubricant and also without having resin coating, e.g. a fluororesin coating, on the surface of the deformable sealing element. Thereby, an injector with the stopper of the invention will provide a smoother experience to an end user compared to a stopper not having the cavity. The stopper body has an access diameter. In the context of the invention, the "access diameter" corresponds to the diameter of a piston rod appropriate for use with the stopper when inserted into the cylinder of an injector.

Experiments by the inventor show that the outward force exerted from a known stopper via its sealing element and onto the container inner wall is commonly far in excess of what is needed to achieve sufficient sealing during storage and ultimately injection of a patient. Sealing ability, also known as container closure integrity (CCI), is a parameter to be carefully aware of with regards to construction of any injection system. However, the present invention shows that it is possible to eliminate excess force while maintaining the necessary degree of CCI.

According to the invention the objective of reducing the excessive and adverse forces exerted from the stopper via the deformable sealing element and towards the container inner wall can be achieved by the stopper design according to the invention. By implementation of the stopper of the invention the static and mean forces against the container inner wall are substantially reduced thereby highly improving the performance of the complete injection system.

The stopper has a stopper body and a deformable sealing element. The deformable sealing element has a diameter, which is larger than the transverse diameter of the stopper body. The stopper is for an injector for delivery of a pharmaceutical composition, and such an injector will comprise a cylinder having an inner wall and an inner diameter. The diameter of the deformable sealing element is larger than the inner diameter of the cylinder where the stopper is employed. When the stopper is inserted into a cylinder of the injector, the deformable sealing element seals an annular gap between the stopper body and the inner wall of the cylinder. In general, the stopper body will not be in direct contact with the inner wall of the cylinder. Thus, the stopper body and the deformable sealing element may be made from a single material or from different material, or the stopper body may alone be made from different materials. Sections of the stopper not in contact with the inner wall of the cylinder may be considered to represent the stopper body, and sections of the stopper in contact with the inner wall of the cylinder may be considered to represent the deformable sealing element. In a specific embodiment, the stopper comprises two or more deformable sealing elements, which may both have a cavity at their corresponding locations. For example, the stopper may comprise a first deformable sealing element at a first axial location from the actuating surface and a cavity at the first axial location and a second deformable sealing element at a second axial location from the actuating surface and a second cavity at the second axial location. When the stopper comprises two or more deformable sealing elements the distance between the deformable sealing elements will generally be in the range of 50% to 80% of the axial length of the stopper, e.g. the distance will be in the range of 1 mm to 6 mm, such as about 5 mm. When the stopper comprises two or more deformable sealing elements with cavities, the cavities may be separate or the same cavity may extend from the first axial location to the second axial location so that the deformable sealing elements can be said to "share" the cavity. Thus, the stopper may comprise a first deformable sealing element at a first axial location from the actuating surface and a second deformable sealing element at a second axial location from the actuating surface and a cavity extending between the first axial location and the second axial location. In a particular embodiment, the stopper comprises a toroidal cavity extending between the first axial location of a first deformable sealing element and the second axial location of a second deformable sealing element. When several deformable sealing elements share a cavity, the manufacture of the stopper is simplified compared to a stopper having multiple separate cavities. Moreover, with two or more deformable sealing elements better control of CCI is obtained while the stopper also has a low BLF after insertion into the cylinder of an injector, which is especially relevant for prefilled injector since leakage is prevented over extended periods of time, e.g. more than a week.

The stopper, i.e. the stopper body and the deformable sealing element, may be made from any appropriate material. In particular, the deformable sealing element will be appropriately elastic for the deformable sealing element to seal the annular gap when inserted into the cylinder of an injector. The stopper, e.g. the stopper body, or the stopper body and the deformable sealing element, may for example be made from an elastic polymer, e.g. a TPE. In a certain embodiment the stopper is injection moulded from a TPE, e.g. a styrene block copolymer (SBC), such as SBC selected from the list consisting of hydrogenated SBC or non-hydrogenated SBS or alloys of these. It is especially preferred that the stopper including the stopper body and the deformable sealing element is injection moulded as a single piece from a TPE. A particularly preferred material for the deformable sealing element, and in particular for the deformable sealing element and the stopper body injection moulded as a single piece, is a TPE having a Shore A hardness in the range of 30 to 90, and even more preferred is a Shore A hardness in the range of 50 to 90, e.g. 60 to 80. When the deformable sealing element is a TPE with a Shore A hardness in the range of 30 to 90 the effect of the cavity is on the reduction of the BLF is so pronounced that the stopper can be used without external lubrication. In this context, external lubrication includes any form of lubrication, in particular silicone oils, silicone baked on the inner surface of the cylinder of an injector, perfluoro polymers or other laminated polymers on either the surface of the stopper or the inner surface of the cylinder of an injector. Thus, TPE material of the deformable sealing element will be in direct contact with the inner surface of the cylinder of an injector after insertion of the stopper into the cylinder. The present inventor has, in particular, observed that an injector with a stopper of the invention with the deformable sealing element made from the TPE can be used with a pharmaceutical composition that does not comprise lubricating ingredients. However, the BLF will be lowered regardless of the presence of a lubricant, and in particular when the deformable sealing is made from other materials than TPE, e.g. a butyl rubber, an injector with the stopper may also comprise a lubricant.

Any TPE may be used for the stopper of the invention, e.g. for the deformable sealing element and also the stopper body. Appropriate TPEs comprise SBCs, e.g. hydrogenated—H—SBC—(SEBS—styreneethylene butylenes-styrene or similar) or non-hydrogenated (SBS—styrene-butadienestyrene) or alloys of these and other compatible polymers, such as COC elastomers, or styrene-butadiene (SB), styrene-isoprene-styrene (SIS), styrene-isoprene-butadiene-styrene (SIBS), styrene-ethylene-ethylene-propylene-styrene (SEEPS) or alloys of any of these compounds. Preferred SBCs are those known under the trademark Evoprene as marketed by AlphaGary Corporation (Leominster, Mass., USA), and Mexichem Specialty Compounds. Evoprenes are described in the brochure "EVOPRENE™ Thermoplastic Elastomer (TPE) Compounds-GENERAL INFORMATION" (published by AlphaGary, July 2007), and preferred Evoprene™ polymers are Evoprene™ Super G, Evoprene™ G, Evoprene™ GC, and Evoprene™ HP, which are described in the brochures "EVOPRENE™ SUPER G Thermoplastic Elastomer (TPE) Compounds", "EVOPRENE™ G Thermoplastic Elastomer (TPE) Compounds", "EVOPRENE™ GC Thermoplastic Elastomer (TPE) Compounds", and EVOPRENE™ HP Thermoplastic Elastomer (TPE) Compounds (published by AlphaGary, July 2007), respectively. The contents of all mentioned brochures by AlphaGary are hereby incorporated by reference. Other relevant elastomers comprise COC elastomers, e.g. TOPAS® Elastomer E-140. The TPE may be selected based on the gas, e.g. oxygen, permeability, and in general it is preferred, especially for a stopper for a prefilled syringe, that the gas permeability is as low as possible. SIBS TPEs generally have very low gas permeabilities and these are therefore appropriate for stoppers for prefilled syringes.

When the stopper is injection moulded the stopper can be made with lower tolerances than afforded by technologies such as vulcanisation, which is commonly used in the manufacture of traditional rubber pistons, e.g. pistons made from bromobutyl or chlorobutyl rubber. However, the stopper is not limited to TPEs, and other appropriate materials comprise elastomers, such as rubbers, e.g. natural rubber, synthetic rubber (polyisoprene rubber, butyl rubber), silicone rubber, and the like, which may be defined with respect to e.g. the Shore durometer, which indicates the elasticity of the elastomeric material and measures the hardness of the elastomeric material, where the higher the durometer, the harder the compound. For example, in an embodiment of the invention the stopper, e.g. including a deformable sealing element, has a Shore A hardness in the range of 30 to 90, e.g. 50 to 90, preferably 60 to 80, more preferred 70 to 76. The terms "Shore hardness" and "Shore durometer" may be used interchangeably. In general, the deformable sealing element will be homogeneous and composed of the same material throughout the volume of the deformable sealing element, which material has a Shore A hardness in the given ranges. By using a material with a Shore A hardness in the above mentioned range, a relatively hard elastomeric material is provided. It should be noted that Shore A durometer is only one of many ways to characterise the material properties of the chosen material, and that other tests may also be employed to characterise the material. Measurement of the Shore A hardness is well-known to the skilled person and in particular the Shore A hardness is generally recorded according to the ISO 868 standard.

Exemplary TPE's and their Shore A hardnesses are summarised in Table 1.

TABLE 1

| Exemplary TPE's | | | | | |
|---|---|---|---|---|---|
| Evoprene G 3295 | 57 | Evoprene GC 5648 | 55 | Evoprene GC 5700 | 75 |
| Evoprene G 6087 | 86 | Evoprene GC 5649 | 63 | Evoprene GC 5701 | 86 |
| Evoprene G 614 | 88 | Evoprene GC 5650 | 71 | Evoprene GC 640 | 80 |
| Evoprene G 927 | 82 | Evoprene GC 5651 | 76 | Evoprene GC 641 | 76 |

TABLE 1-continued

Exemplary TPE's

| | | | | | |
|---|---|---|---|---|---|
| Evoprene G 940 | 87 | Evoprene GC 5652 | 87 | Evoprene GC 642 | 76 |
| Evoprene G 958 | 56 | Evoprene GC 5656 | 54 | Evoprene GC 645 | 86 |
| Evoprene G 962 | 50 | Evoprene GC 5657 | 60 | Evoprene HP 3704 | 50 |
| Evoprene G 963 | 60 | Evoprene GC 5658 | 69 | Evoprene HP 3706 | 60 |
| Evoprene G 964 | 88 | Evoprene GC 5659 | 76 | Evoprene HP 3708 | 70 |
| Evoprene G 969 | 65 | Evoprene GC 5681 | 59 | Evoprene HP 3710 | 80 |
| Evoprene G 970 | 70 | Evoprene GC 5682 | 67 | Evoprene HP 3712 | 90 |
| Evoprene G 971 | 83 | Evoprene GC 5683 | 76 | Evoprene HP 3724 | 50 |
| Evoprene G 974 | 71 | Evoprene GC 5684 | 85 | Evoprene HP 3726 | 60 |
| Evoprene G 975 | 84 | Evoprene GC 5688 | 53 | Evoprene HP 3728 | 70 |
| Evoprene G 978 | 91 | Evoprene GC 5689 | 61 | Evoprene HP 3730 | 80 |
| Evoprene G 991 | 60 | Evoprene GC 5690 | 67 | Evoprene HP 3732 | 90 |
| Evoprene G 996 | 74 | Evoprene GC 5691 | 78 | Evoprene Super G 931 | 61 |
| Evoprene GC 5617 | 59 | Evoprene GC 5692 | 83 | Evoprene Super G 932 | 71 |
| Evoprene GC 5618 | 65 | Evoprene GC 5693 | 86 | Evoprene Super G 934 | 76 |
| Evoprene GC 5619 | 73 | Evoprene GC 5698 | 52 | Evoprene Super G 949 | 54 |
| Evoprene GC 5647 | 50 | Evoprene GC 5699 | 63 | TOPAS ® E-140 | 89 |

A TPE may also be defined by its compression set value, which corresponds to the deformation remaining after removal of a force that was applied to it (and is typically expressed in %). The compression set value is typically recorded over a specified period of time, e.g. in the range of 18 hours to 96 hours or 22 to 72 hours, and at a specified temperature, for example according to the ISO 815 standard. In the context of the present invention the compression set is generally recorded at an "ambient temperature", e.g. in the range of 10° C. to 40° C. However, the temperature range may also extend beyond ambient temperature, e.g. 23° C. to 100° C. In general, the higher the temperature the shorter the time relevant for recording the compression set. The compression set should generally be as low as possible but for a stopper, or a part of a stopper, of the invention the compression set may be in the range of 15% to 40%, e.g. at ambient temperature. At higher temperatures, e.g. 100° C., the compression set will typically be higher, e.g. up to 50%. It is, however, preferred that the compression set at ambient temperature is in the range of 10% to 40%. The compression set value is generally relevant for prefilled injectors where the stopper will be inserted into the cylinder and therefore compressed when the prefilled injector is stored for extended periods of time. When the stopper, e.g. the stopper body and also the deformable sealing element, has a Shore A hardness in the range of 30 to 90, e.g. 50 to 90, and a compression set value of at least 25%, e.g. in the range of 25% to 35%, the BLF of a prefilled injector of the invention will decrease upon storage, e.g. for at least 5 days, so that a stopper of the invention is especially advantageous for a prefilled injector. As long as the compression set is below 40% at ambient temperature, CCI is ensured.

When the deformable sealing element is not deformed, e.g. when the stopper is not inserted into an injector, the deformable sealing element is considered to be in a "relaxed state", e.g. in a state without deformation. The material of the stopper body is not required to be elastic, and any material may be chosen for the stopper body. In an embodiment, the material of the stopper body is different from the material of the deformable sealing element. In another embodiment, the material of the stopper body is the same as the material of the deformable sealing element. For example, the stopper, i.e. the stopper body and the deformable sealing element, may be injection moulded as a single piece.

In the context of the invention, the "deformable sealing element" may describe any section of the stopper, which has a diameter larger than the transverse diameter of the stopper body. In the context of the invention, the term "diameter" does not imply that the corresponding element, e.g. the stopper body or the deformable sealing element, must have a circular cross-section, i.e. the cross-section in the lateral plane of the stopper, and any cross-sectional shape as desired may be used for the stopper body and/or the deformable sealing. For example, the cross-section may be polygonal, e.g. triangular, square, pentagonal, hexagonal, etc., and the term diameter will in this case refer to a cross-sectional dimension, e.g. the largest cross-sectional dimension for the corresponding cross-sectional shape. A polygonal cross-section is not limited to polygons having equal angles and side lengths, i.e. regular polygons, and likewise the cross-section may also be elliptical. The cross-sectional shape of the cylinder of an injector will correspond to the cross-sectional shape of the deformable sealing element. The stopper body does not interact with the inner wall of the cylinder, and the cross-sectional shape of the stopper body can be chosen freely, regardless of the cross-sectional shape of the deformable sealing element.

The stopper of the invention has a deformable sealing element, which deformable sealing element, when the stopper is inserted in the cylinder, abuts the inner wall of the cylinder at an abutting interface and seals an annular gap between the stopper body and the inner wall of the container, the abutting interface and the deformable sealing element having axial dimensions parallel with the longitudinal axis. The deformable sealing element is located at an axial location from the actuating surface, and a cavity is also located at the axial location. The cavity can therefore be considered to be located at the same location as the deformable sealing element, and the cavity may also be referred to as a "sealing element cavity", and its location can be said to be opposite the deformable sealing element. At this location, the cavity thereby reduces the force between the deformable sealing element and the container inner wall achieving a significant reduction of force needed to move the stopper and allowing a complete removal of any lubrication means including but not limited to any coating, any liquid lubricant and or baked-on silicone between the sealing element and the inner wall of the container.

The deformable sealing element is preferably convex. In this context, the term "convex" means that a straight line between any two points within the deformable sealing element does not cross the surface of the deformable sealing element. Any convex shape is contemplated, but the deformable sealing element preferably has a point, e.g. a point in an axial plane of the stopper, representing the maximal extension from the centre axis of the stopper. When the deformable sealing element has a convex surface the force exerted via the deformable sealing element on the inner wall of the container will be maximised, since deformation of the deformable sealing element in a direction of the longitudinal axis of the cylinder is minimised. The contact may for example be at an abutting interface between the deformable sealing element and the inner wall of the cylinder. It is preferred that the extent of the contact between the deformable sealing element and the inner wall of the cylinder of an injector into which the stopper has been inserted is as small as possible. For example, when the stopper of the invention is inserted into a cylinder of an injector, an abutting interface will form at the inner wall of the cylinder, and for the abutting interface the ratio between the largest axial dimension of the abutting interface and the largest axial dimension of the deformable sealing element is preferably in the range of 0.01 and 0.4, e.g. between 0.01 and 0.2, between 0.01 and 0.15, between 0.01 and 0.1, between 0.01 and 0.05. For example, the convex deformable sealing element, i.e. in a relaxed state, may have an axial extension in the range of 5% to 25% of the axial length of the stopper body, e.g. an axial extension in the range of 0.5 mm to 2 mm, and an outer diameter in the range of 105% to 120% larger than the transverse diameter of the stopper body. The deformable sealing element may further be defined by angles between the stopper body and the deformable sealing element, and these angles may be in the range of 120° to 160° when the convex deformable sealing element has an axial extension in the range of 5% to 25% of the axial length of the stopper body. For example, the outer diameter may be in the range of 4.75 mm to 5.15 mm for a 0.5 mL injector having a cylinder with an inner diameter of 4.65 mm, the outer diameter may be in the range of 6.5 mm to 7 mm for a 1 mL injector having a cylinder with an inner diameter of 6.35 mm or the outer diameter may be in the range of 8.80 mm to 9.35 mm for a 2.25 mL injector having a cylinder with an inner diameter of 8.65 mm. When the stopper has been inserted into a cylinder of an injector contact angles will form between the inner wall of the cylinder and the deformable sealing element. There will thus be a contact angle facing the actuating surface of the stopper and a contact angle facing the outlet surface of the stopper and these contact angles can be referred to as the "actuating contact angle" and the "outlet contact angle", respectively. In an embodiment, the actuating contact angle is approximately identical to the outlet contact angle, although the actuating contact angle may also be different from the outlet contact angle. For example, the contact angles may be in the range of 5° to 60°, e.g. 15° to 45°. When the contact angles are in the range of 5° to 60° the deformable sealing element will be convex also after the stopper has been inserted into the cylinder. This allows that the sealing effect of the deformable sealing element is maximised, which is especially relevant when the outer diameter of the deformable sealing element is 1.5% to 10% larger, e.g. 2% to 5% larger, than the inner diameter of the cylinder, since the container closure integrity (CCI) is ensured. In an embodiment, the stopper, i.e. including the deformable sealing element, is injection moulded from a TPE, and the deformable sealing element is convex and has an outer diameter in the range of 1.5% to 5% larger than the inner diameter of the cylinder, when the stopper is in a relaxed state, and when the stopper is inserted into the cylinder of an injector, the actuating contact angle and the outlet contact angle are, independently, in the range of 5° to 45°.

The stopper body has an actuating surface opposite an outlet surface. The actuating surface and the outlet surface are thus located at opposite ends, i.e. opposite ends in an axial dimension, of the stopper body. The actuating surface may also be said to be at an actuating end of the stopper body, and the outlet surface may also be said to be at an outlet end of the stopper body. When inserted into the cylinder of an injector, the outlet end of the stopper body faces the outlet of the injector.

The deformable sealing element has an axial extension. The axial extension may be defined by the distance between the points where the diameter of the deformable sealing element is larger than the diameter of the stopper body. The deformable sealing element may have an axial extension in the range of 5% and 95% of the axial length of the stopper body, and the deformable sealing element may be located anywhere on the stopper body. In a preferred embodiment, the axial extension of the deformable sealing element is in the range of 20% and 50% of the axial length of the stopper body.

The deformable sealing element is located at an axial location from the actuating surface of the stopper body. The term "axial location" refers to a point, e.g. a point in an axial plane of the stopper, defined by the axial extension of the deformable sealing element. In general, the axial location will be the midpoint between the points where the diameter of the deformable sealing element is larger than the diameter of the stopper body. However, in an embodiment the deformable sealing element is convex and has a point representing the maximal extension from the centre axis of the stopper, e.g. the maximal diameter of the deformable sealing element. When the deformable sealing element is convex and has a point representing the maximal extension from the centre axis of the stopper, the axial location can be defined by the axial distance from the actuating surface to the location of the maximal extension. Thus, when the deformable sealing element has a maximal extension, i.e. a single maximal extension, from the centre axis of the stopper, e.g. when the deformable sealing element is convex, the location of the maximal extension from the actuating surface represents the axial location.

The stopper comprises a cavity at the axial location of the deformable sealing element. In the context of the invention, a "cavity" comprises a compressible material, e.g. a compressible fluid, in particular air or a gas, surrounded by the material of the stopper, optionally also including the material of a piston rod. Thus for example, the cavity may be contained, e.g. fully contained, in the deformable sealing element, e.g. in the material of the deformable sealing element, or the stopper body, e.g. the material of the stopper body. For example, the cavity may be a gas enclosed by the material of the deformable sealing element or the material of the stopper body. The cavity may also be a gas enclosed by the material of the stopper body. In other embodiments, the cavity is formed at an interface between the stopper body and the deformable sealing element, e.g. between the material of the stopper body and the material of the deformable sealing element. In yet another embodiment, the cavity is formed at an interface between the material of the deformable sealing element and a piston rod, e.g. the piston rod may provide the stopper body. In a specific embodiment, the stopper body and the deformable sealing element are made as a single piece formed from the same material, i.e. the "stopper material". In this embodiment, the cavity may be enclosed by the stopper material, or the cavity may be formed at an interface between the stopper material and a piston rod.

The cavity may have any size, e.g. volume, and shape. The cavity may be a single cavity or the cavity may comprise any number of smaller subcavities, e.g. the cavity may be a "foam". When the cavity comprises smaller subcavities, the totality of the subcavities will be referred to with respect to the size, shape and volume as a single cavity comprising the subcavities. The cavity may be a volume of air included in, and thereby enclosed by, the stopper material or by the deformable sealing element. For example, the stopper may be injection moulded as single piece, i.e. a single piece comprising the stopper body and the deformable sealing element, and bubbles of air may be included in the injection moulding to form the cavity. In particular, the pressure of the air may be adjusted taking into account the temperature of the injection moulding so that cooling of the injection moulded stopper will result in formation of appropriately sized cavities in the final stopper.

The cavity, e.g. a cavity enclosed by the stopper material, may have any desired shape. For example, the cavity may be spherical, ellipsoidal, egg shaped, or cylindrical. In specific embodiments, the cavity is spherical, ellipsoidal, egg shaped, or cylindrical and has a lateral extension, e.g. a diameter or a major axis, in a lateral plane of the stopper. The cavity has a lateral extension, e.g. a lateral diameter. The lateral extension is larger than the access diameter of the stopper body. The access diameter of the stopper body is sufficient to house a piston rod for actuating the stopper after insertion into the cylinder of an injector. The present inventor has found that when a cavity having an extension, in particular a diameter, smaller than the access diameter of the stopper body, the presence of the cavity did not provide any effect on the BLF of the stopper, regardless of the presence of a lubricant. However, when the lateral extension of the deformable sealing element was larger than the access diameter, the BLF was lowered to an extent where the stopper could be used without any lubrication, including a fluororesin coating on the deformable sealing element. The effect was observed both when a cylindrical cavity was formed between the piston rod and the surface of the stopper material or when a toroidal cavity was formed between the piston rod and the surface of the stopper material, e.g. the piston rod was fully inserted into the stopper. The lateral diameter is preferably in the range of 50% to 65%, e.g. in the range of 60% to 65%, of the outer diameter of the deformable sealing element.

In a specific embodiment, the cavity has a generally toroidal shape, and the toroidal shape may also be described with a lateral extension, e.g. a lateral diameter or a lateral major axis, in a lateral plane of the stopper. When the cavity is toroidal, the lateral extension will refer to the extension without the core of the toroid. For example, the toroid may surround the stopper body so that the toroid has a core corresponding to the axial extension, e.g. the diameter, of the stopper body, e.g. the access diameter. The stopper body will generally have a diameter in the range of 50% to 90% of the outer diameter of the deformable sealing element. The depth of the toroid, e.g. from the surface of the stopper body, will generally be in the range of 10% to 30% of the outer diameter of the deformable sealing element. The cavity, e.g. a spherical, ellipsoidal, egg shaped, or cylindrical cavity, will also have an axial extension in the axial direction of the stopper, e.g. an axial length, and the axial length may be in the range of 5% and 95%, e.g. 5% to 50%, or 10% to 20%, of the axial length of the stopper body, e.g. when the stopper is in a relaxed state.

In a further embodiment the cavity comprises a compressible material, such as a sponge or the like. For example, the material, e.g. an elastic material, may have a network of a regular or irregular structure with the material making up from 10% to 40% of the total volume of the structure. A stopper having such a structure comprising different materials, e.g. two materials, may be prepared by two-component moulding.

In a preferred embodiment the stopper, i.e. the stopper body and the deformable sealing element, is provided as a single piece of material in its final shape. Such a material may be provided by injection moulding of a TPE. It is especially preferred that the stopper is injection moulded as a single piece in its final shape from a TPE having a Shore A hardness in the range of 30 to 90, e.g. 50 to 90, e.g. 70 to 90. This stopper is appropriate for an injector not containing a lubricant, e.g. a silicone lubricant.

In other embodiments, the cavity is formed at an interface between elements of the stopper or elements of the stopper and a piston rod. For example, the stopper body may comprise a solid and rigid material, e.g. the stopper body may be a piston rod, in particular the diameter of the piston rod may define the access diameter of the stopper body, and the deformable sealing element may be an O-ring with a recess along the inner diameter of the O-ring so that upon mounting of the O-ring on the stopper body, e.g. the piston rod, the cavity will be formed between the O-ring and the stopper body at the recess, thereby forming a toroidally shaped cavity. In a specific embodiment, the stopper body of the stopper of the invention is part of a piston rod or is a piston rod, and the deformable sealing element is an O-ring made from a TPE having a Shore A hardness in the range of 30 to 90, the O-ring having a recess along the inner diameter of the O-ring. The diameter of the stopper body part of the piston rod may be in the range of 10% to 90%, e.g. 30% to 70%, of the inner diameter of an injector appropriate for the stopper with the piston rod. The inner diameter of the O-ring is smaller than an outer diameter of the stopper body part of the piston rod so that the O-ring is securely mounted on the stopper body part of the piston rod and the cavity is formed as a toroid between the stopper body and the inner surface of the O-ring, i.e. at the recess, upon mounting of the O-ring on the stopper body. The surface of the stopper body part of the piston rod may have a groove for ensuring that the O-ring is stably mounted on the stopper body. The material of the O-ring may have a diameter in the range of 0.2 mm to 2 mm, and the recess may have a depth in the range of 20% to 80% of the diameter of the O-ring. In a further embodiment, the piston rod comprises two or more O-rings as defined above.

In a further embodiment, the stopper body has a cylindrical shape, e.g. a cylindrical shape defining the access diameter, and the deformable sealing element is comprised on a cylindrical structure, e.g. a "sleeve", for mounting on the stopper body, so that upon mounting of the cylindrical structure on the stopper body, the cavity will be formed between the surface of the stopper body and the inner surface of the cylindrical structure. The cylindrical structure has an inner surface, and the inner surface may contain a recess at the axial location of the deformable sealing element and/or the surface of the stopper body may contain a recess at the axial location of the deformable sealing element. Thereby, a toroidal cavity will be formed at the recess or the recesses between the stopper body and the cylindrical structure. The "depth" of the toroid, i.e. the distance from the surface of the stopper body to the surface of the cylindrical structure when the cylindrical structure is mounted on the stopper body, will generally be in the range of 10% to 30% of the outer diameter of the deformable sealing element. It is preferred that the cylindrical structure comprises two, three or more deformable sealing elements. The stopper body may be part of a piston rod, and it is preferred that the stopper body is made of a hard material, e.g. a thermoplastic polymer. The stopper body may have a lateral diameter in the range of 10% to 90%, e.g. 30% to 70%, of the inner diameter of an injector appropriate for the stopper. The cylindrical structure is preferably made from an elastic material, e.g. it may be injection moulded from a TPE, in particular a TPE having a Shore A hardness in the range of 30 to 90, e.g. 50 to 80.

The stopper may have a tubular section for housing a piston rod. The piston rod may comprise the stopper body. The diameter of the tubular section or the diameter of the piston rod will generally define the access diameter of the stopper body. In this embodiment, the cavity can be formed, e.g. as a toroidal cavity, in the interface between the stopper body, e.g. the piston rod, and the deformable sealing element. In a specific embodiment, the stopper including the deformable sealing element is formed as a single piece, e.g. by injection moulding, and the stopper body has a tubular section for housing a piston rod. The stopper material is preferably a TPE, e.g. a styrene block copolymer (SBC). The piston rod may have any size and shape allowing the piston rod to be inserted into the tubular section and actuate, e.g. push, the stopper. One end of the piston rod has an engagement section with a terminal site and an outer surface defining an outer diameter. The tubular section has an inner surface defining an inner diameter sized to house the engagement section. The inner diameter of the tubular section may be approximately equal to or smaller than the outer diameter of the engagement section. In particular, when the inner diameter of the tubular section is smaller than the outer diameter of the engagement section the stopper material should be elastic, e.g. the stopper can be injection moulded from a TPE. Thereby, insertion of the engagement section into the tubular section can form a cavity at the interface between the terminal site of the engagement section and the tubular section and/or between the inner surface of the tubular section and the outer surface of the engagement section.

The tubular section extends from the actuating surface to a bottom of the tubular section beyond the axial location of the deformable sealing element. Thereby, upon insertion of the piston rod into the tubular section, the cavity can be formed at the axial location between the outer surface of the engagement section and the inner surface of the tubular section and/or between the terminal site of the engagement section and the bottom of the tubular section. For example, the piston rod may be inserted into the tubular section so that the terminal site is in contact with the bottom of the tubular section, and a toroidal cavity is formed, e.g. is enclosed, between the outer surface of the engagement section and the inner surface of the tubular section. In another embodiment, the piston rod is inserted into the tubular section so that a cavity is formed between the terminal site of the engagement section and the bottom of the tubular section; this cavity may have a cylindrical or ellipsoidal shape. Any combination of the toroidal, cylindrical and ellipsoidal shapes is also possible by controlling how far into the tubular section the piston rod is inserted.

In order to control how far into the tubular section, the piston rod can be inserted, the piston rod may comprise a ridge or the like. The ridge may have any shape desired, but the ridge will generally be located adjacent to the engagement section. Thereby it is ensured that the engagement section can be inserted into the tubular section to a distance where the cavity formed between the inner surface of the tubular section and the outer surface of the engagement section and/or between the terminal site and the bottom of the tubular section has a predefined size and shape. The ridge may fully surround the piston rod, or the ridge may comprise two, three or more elements extending from the centre axis of the piston rod. Whatever the shape of the ridge, the ridge will have an extension, e.g. a diameter, smaller than the inner diameter of the cylinder of the injector and larger than the inner diameter of the tubular section.

In specific embodiments, the tubular section comprises an engagement device for engaging a complementary engagement device of the engagement section. The engagement device and the complementary engagement device may be chosen freely, but engagement of the engagement device with its complementary engagement device allows that the piston rod can both push and pull the stopper and thus an injector with the stopper and the piston rod can be filled and emptied by moving the piston up and down in the injector, respectively. In an embodiment, the engagement section has an external thread, e.g. a helical external thread, and the tubular section correspondingly comprising a complementary internal thread, e.g. a helical internal thread, the threads thus provide the engagement device and the complementary engagement device, respectively. An internal helical thread will have a larger and a smaller diameter, which together define the helix. The smaller diameter will define the access diameter of the stopper body. When the engagement section comprises an external thread the piston rod, especially the engagement section, is preferably made from a non-elastic material, e.g. a thermoplastic polymer. The inner surface of the tubular section with the complementary internal thread may also be made from a non-elastic material, e.g. a thermoplastic polymer. However, as long as the external thread is made from a non-elastic material, the internal thread, in particular the tubular section or the tubular section and the deformable sealing element, can be made from an elastic material, in particular a TPE.

When the stopper body comprises a tubular section, the bottom may also comprise additional structures, e.g. to provide specific shapes to the cavity. For example, the bottom of the tubular section may comprise a protrusion having an upper surface that can be brought into contact with the terminal site of the engagement section so that a cavity is formed between the surface of the protrusion and the inner surface of the tubular section. The protrusion may also be referred to as a solid portion. The protrusion may be a cylindrical protrusion with a smaller diameter, e.g. which smaller diameter defines the access diameter, than the inner diameter of the tubular cavity so that the formed cavity will have the shape of a cylindrical shell. The protrusion may also have other shapes. For example, the protrusion may comprise further structures between the surface of the protrusion and the inner surface of the tubular section so that several subcavities can be formed upon insertion of the engagement section into the tubular section. e.g. the cavity will have the shape of an interrupted cylindrical shell. For example, the stopper may comprise a protrusion with two, three, four or more elements extending from the protrusion to the inner surface of the tubular section to create two, three, four or more subcavities, respectively. When the bottom of the tubular section comprises additional structures the stopper is preferably injection moulded as a single piece comprising the deformable and the stopper body having the tubular section with the protrusion in the bottom of the tubular section.

The stopper of the invention will have at least one deformable sealing element and the stopper will have a cavity at the axial location of this at least one deformable sealing element. However, the stopper may also comprise further deformable sealing elements. When the stopper has more than one, e.g. two or three deformable sealing elements, each deformable sealing element will be at an axial location from the actuating surface. The stopper may have one or more cavities, and at least one cavity will be at an axial location of a deformable sealing element. For example, the stopper may have a first deformable sealing element at a first axial location from the actuating surface and a second deformable sealing element at a second axial location from the actuating surface. The stopper may have a first cavity at the first axial location from the actuating surface and optionally also a second cavity at the second axial location from the actuating surface. In the context of the invention, the first axial location is, unless noted otherwise, the axial location closest to the outlet surface of the stopper body. Any embodiment of the cavity described above is relevant at the first axial location when the stopper comprises additional deformable sealing elements.

In an embodiment, the stopper has a second deformable sealing element at a second axial location from the actuating surface of the stopper body, and a second cavity at the second axial location. The stopper body may be solid and both cavities may be enclosed by the material of the stopper body. In a specific embodiment, the stopper, in particular a stopper injection moulded as a single piece of TPE, comprises a tubular section extending from the actuating surface to a bottom of the tubular section beyond the first and the second axial locations of the deformable sealing elements. The stopper in this embodiment is to be used with a piston rod having an engagement section as defined above. The first cavity at the first axial location, i.e. the axial location closest to the outlet surface of the stopper body, may have any size and shape as defined above, and the second cavity will be formed at the interface between the outer surface of the engagement section and the inner surface of the tubular section. Thus, the second cavity will be of a generally toroidal shape, whereas the first cavity may be toroidal, ellipsoidal, cylindrical or a combination thereof. The piston rod for this embodiment preferably has a ridge as defined above.

In a further embodiment, the stopper body comprises an actuating stopper element and an outlet stopper element, which actuating stopper element and outlet stopper element are linked together by a resilient frame. The resilient frame may have any design but in a specific embodiment, the resilient frame has the overall shape of a ring. When the stopper having the resilient frame is inserted into the cylinder of an injector and the actuating stopper element is pushed the resilient frame will push the outlet stopper element, and when the actuating stopper element is pulled the resilient frame will pull the outlet stopper element. Each of outlet stopper element and the actuating stopper element has a deformable sealing element as defined above, and the outlet stopper element and the actuating stopper element are located at a first and a second axial location from the actuating surface of the stopper body, respectively, and the stopper has a first and optionally also a second cavity at the first and second axial locations, respectively. The diameters of the cavities will typically, independently, be in the range of 50% to 65% of the outer diameter of the deformable sealing elements. The stopper, including the outlet stopper element and the actuating stopper element and the resilient frame are preferably injection moulded as a single piece, e.g. from a TPE. Preferred materials for the actuating stopper element, the outlet stopper element, and the resilient frame, are TPE's, e.g. an SBC, such as an SBC selected from the list consisting of hydrogenated SBC or non-hydrogenated SBS or alloys of these. It is further preferred that the actuating stopper element, the outlet stopper element and the resilient frame are injection moulded from a TPE as a single piece. In an embodiment the actuating stopper element, the outlet stopper element, the resilient frame, or the actuating stopper element, the outlet stopper element and the resilient frame have a Shore A hardness in the range of 30 to 90, e.g. 50 to 90. When the resilient frame has a Shore A hardness in the range of 50 to 90, in particular 70 to 90.

When the stopper having the resilient frame is inserted into the cylinder of an injector, the deformable sealing elements of both the actuating stopper element and the outlet stopper element abut the inner wall of the cylinder and seal a gap between the inner wall of the cylinder and the stopper body thereby creating a compressible section between the actuating stopper element and the outlet stopper element. The resilient frame will typically have a volumetric fraction in the range of 10% to 90%, e.g. 10% to 70%, 15% to 50%, or 20% to 40%, of the volume of the compressible section, e.g. when the stopper is in a relaxed state, and the remainder may be constituted by a compressible fluid, e.g. air or air with liquid droplets, such as droplets of water formed due to the humidity of the air. The axial length of the compressible section will typically be in the range of 10% to 90% of the total axial length of stopper in a relaxed state, such as at least 20%, e.g. at least 25% or at least 30% of the total axial length of the stopper. For example, the resilient frame may have a length in the range of 30% to 70%, e.g. such as 30%, 40%, 50%, 60% or 70%, of the length of the stopper in a relaxed state. By linking the actuating stopper element with the outlet stopper element via the resilient frame, the overall BLF may be aligned with and have a value similar to the glide force of the stopper. This provides an even smoother experience to the end user of an injector with the stopper, than can be obtained using a stopper of the invention having two deformable sealing elements with cavities according to the invention. Further details for stoppers with a resilient frame are disclosed in WO 2017/157396, which is hereby incorporated by reference.

In a specific embodiment, the resilient frame has a cylindrical shape. For example, the stopper may be injection moulded as a single piece, e.g. from a TPE, to have the actuating stopper element and the outlet stopper element and a tubular section where at least a part of the tubular section between the actuating stopper element and the outlet stopper element has a reduced wall thickness so that there cannot be contact between the engagement section of a piston rod inserted into the tubular section. For example, the wall thickness is such that the tubular section, i.e. the resilient frame, has a volumetric fraction in the range of 10% to 25% of the volume of the compressible section. Without contact between the engagement section and the walls of the tubular section, the walls of the tubular section will be flexible and allow the actuating stopper element to start moving before the outlet stopper element when the actuating stopper element is pushed, e.g. using a piston rod. Thereby, the cylindrically shaped tubular section will be the resilient frame. In this embodiment it is preferred that a toroidally shaped cavity is formed between the surface of the engagement section and the material of the actuating stopper element. A further cavity will be present at the location of the outlet stopper element. Both cavities will have a reduced BLF compared to piston elements not having cavities, and the resilient frame, in this case the tubular section, will furthermore align the BLF so that little difference between the BLF and the glide force is felt by the end user of an injector having the stopper. For this embodiment it is preferred that the piston rod has a ridge as defined above.

In another embodiment, the stopper with a tubular section also being the resilient frame is used with a piston rod not having an engagement section. For example, the stopper may be used with a piston rod capable of pushing the stopper. In this embodiment the wall thickness of the tubular section is such that the tubular section, i.e. the resilient frame, has a volumetric fraction in the range of 20% to 50%, e.g. 25% to 40%, of the volume of the compressible section.

In yet a further embodiment, the stopper has a tubular section also being the resilient frame as described above, and in an injector the stopper is used with a piston rod having an engagement section with a complementary engagement device to an engagement device of the tubular section. Thereby, the piston rod can both fill and empty an injector with the stopper. For example, the tubular section may have a first inner diameter going through the material of the actuating stopper element from the actuating surface and a larger second inner diameter at the part of the tubular section being the resilient frame, where the site of the change from the first inner diameter to the larger second inner diameter is the engagement device of the tubular section. The piston rod will have an engagement section with a diameter approximately equal the first inner diameter, and a terminal site having a larger cross-section than the first inner diameter. The terminal site will thus serve as a barb that can pull the piston toward the actuating end of an injector with the stopper. The terminal site is thus a complementary engagement device to the engagement device of the tubular section. The terminal site may have any shape as desired. For example, the terminal site may be disc shaped with a diameter larger than the first inner diameter, but smaller than the second inner diameter, or the terminal site may have two or more parts extending from a centre axis of the piston rod to provide a cross-section larger than the first inner diameter.

In another embodiment, the stopper has a cavity at the axial location of a deformable sealing element closest to the outlet end of the stopper, which cavity is open to the outlet end, i.e. at the outlet surface. The stopper may include a tubular section as defined above, in particular, a tubular section having an engagement device for engaging a complementary engagement device of the engagement section of a piston rod. The engagement device and the complementary engagement device may be an internal helical thread and an external helical thread, respectively. The stopper of this embodiment may be used in an injector as it is, since the cavity will reduce the BLF of the stopper compared to a stopper not having the cavity. However, the stopper of this embodiment provides an appropriate starting point for creating a cavity that is enclosed in the stopper body. For example, a tip may be attached to the stopper body so that the cavity is enclosed between the material of the tip and the stopper body. The attachment of the tip to the material of the stopper body may be made as desired. For example, the tip and the stopper body may be glued or welded together. The tip and the stopper body may be of the same or different materials. In a specific embodiment, the stopper, thus including the stopper body and the deformable sealing element, and the tip are made, preferably injection moulded, from a TPE, e.g. from the same TPE, and the tip is attached to the stopper using ultrasonic or laser welding.

In yet another embodiment, the stopper, thus including the stopper body and the deformable sealing element, is injection moulded from a TPE to have tubular section extending from the actuating surface to a bottom located beyond the axial location of the deformable sealing element. The cavity is then formed in the tubular section by attaching a plug in the tubular section so that the cavity is enclosed by the material of the stopper body and the plug. The plug and the stopper may be attached as desired. The plug may fully or partly fill the tubular section. For example, when the tubular section is fully filled by the plug, a stopper can be provided which cannot engage a piston rod, thereby preventing that the piston rod can pull the stopper. The plug may also partly fill the tubular section. This allows that the tubular section can comprise an engagement device for engaging a complementary engagement device of the engagement section of a piston rod, e.g. an internal helical thread and an external helical thread, respectively. The stopper and the plug may be made from the same or different materials. However, it is preferred that the plug is made from a TPE, in particular the same TPE as the stopper. This allows that plug and the stopper are welding together, e.g. using ultrasonic welding or laser welding. In a specific embodiment the stopper body, e.g. at the actuating surface, comprises a depression for facilitating orientation in a vibrational feeder, e.g. a bowl feeder. A depression for facilitating orientation in a vibrational feeder typically does not comprise an internal helical thread. In another embodiment, the actuating surface is symmetrical with the outlet surface. When the actuating surface is symmetrical with the outlet surface it is preferred that surfaces do not comprise any engagement device for engaging a piston rod. In a specific embodiment, the stopper comprises two or more deformable sealing elements, and at least two cavities at the location of two of the deformable sealing elements, and the actuating surface is symmetrical with the outlet surface. However, in another embodiment the actuating surface comprises an engagement device for engaging a complementary engagement device of a piston rod. Any engagement device and complementary engagement device may be used in the invention. In an embodiment, the engagement device comprises an internal helical thread and the complementary engagement device comprises an external helical thread.

The stopper of the invention may be integrated in a piston rod so that the actuating surface will be an actuating end, e.g. a thumb plate, of the piston rod. In a further aspect the invention thus relates to a piston rod for an injector for delivery of a pharmaceutical composition. The piston rod has an integrated version of any embodiment of the stopper of the invention.

The cavity or "sealing element cavity" may be surrounded by solid stopper material in the area towards the outlet end of the stopper and therefore closest to the drug formulation. In general, the larger the cavity dimension perpendicular to the longitudinal axis of the container and stopper and/or the vertical dimension the lower the force exerted via the deformable sealing element on the inner wall and thereby the lower the static and dynamic friction between the deformable sealing element and the container inner wall and, e.g. at the abutting interface.

In a known stopper the lowest deformable sealing element closest to the outlet end of the stopper has the majority of the stopper's sealing capability, since the stopper is solid in the area opposite the lowest deformable sealing element and in the area towards and in contact with the drug formulation. However, the solid portion of elastomeric material opposite the deformable sealing element combined with the larger diameter of the deformable sealing element compared to the inner diameter of the container result in a substantial abutting force at the time of stopper insertion and from then on. The substantial forces involved normally dictate the use of lubrication means in order to be overcome in known stoppers.

According to the present invention the substantial abutting force from the deformable sealing element towards the container inner wall in known stoppers is significantly reduced by implementing a cavity in the stopper solid portion thereby reducing the amount of elastomeric material behind the deformable sealing element ultimately reducing the static and dynamic forces between the sealing element and the container. The stopper of the present invention comprises a sealing element cavity which may be considered to replace the stopper solid portion opposite the deformable sealing element. In its relaxed state before insertion in the container the deformable sealing element comprises a diameter which is larger than the container inner diameter in order to ensure adequate sealing for sufficient container closure after insertion. According to the invention replacement of elastomeric material with a cavity may occur behind any deformable sealing element of a stopper regardless of the deformable sealing element's position on the stopper and hence the deformable sealing element with opposite cavity may be the upper deformable sealing element as well as the lowest deformable sealing element or a middle sealing element or anywhere between the upper and lower deformable sealing element or between the actuating and outlet end of the stopper without restricting the present invention.

The cavity according to the invention may be a full cavity or a partial cavity opposite the sealing element. According to the invention a full cavity has no openings and is hence fully embedded in the stopper body. According to the invention a partial cavity may have an opening in any direction. The cavity opening may be in the direction of the actuating end of the stopper towards the inner thread cavity or connecting means for a piston rod. According to the invention the sealing element cavity will be positioned opposite the deformable sealing element, and the sealing element cavity will have adjacent elastomeric material next to the cavity towards the outlet end of the stopper in the preferred embodiment.

In an embodiment the sealing element cavity will have its opening towards the outlet end of the stopper whereas the closed end and elastomeric material adjacent to the cavity will be towards the actuating section of the stopper.

From the outset the deformable sealing element diameter will be larger than the inner diameter of the container and therefore when inserted in the container the deformable sealing element will exert a peripheral force towards the container inner, e.g. the "basic force". The basic force exerted will be the force deriving from the larger diameter of the sealing element compared to the container inner diameter. The basic force may be relatively small or relatively large, which depends on how the deformable sealing element is supported by elastomeric material opposite the deformable sealing element. The more elastomeric material opposite the deformable sealing element to support it the larger the total force towards the container inner wall.

Conversely, the less elastomeric material behind the deformable sealing element the smaller the force exerted towards the container inner wall. The deformable sealing element's total force towards the container wall is the basic force as a function of deformable sealing element diameter combined with the force causing decreased or increased exertion of force as a function of amount of elastomeric material opposite the deformable sealing element. Conclusively the total force is positively or negatively affected by the amount of elastomeric material exerting the sealing element towards the container inner wall, which will ultimately be a function of the size and dimension of the sealing element cavity.

The sealing element cavity extends so as to define a width inside the stopper along the axis of the deformable sealing element, and extends so as to define a height inside the stopper along the longitudinal axis of the container. And although the height of the sealing element cavity may have an influence on the exertion of power towards the container inner wall especially the width along the same axis as the deformable sealing element will have the majority of effect with regards to the exertion of force towards the container inner wall. The larger width and height the lesser elastomeric material resulting in reduced sealing element abutting force. Conversely the smaller width and height the more elastomeric material resulting in increased sealing element abutting force.

In an embodiment the sealing element cavity is fully surrounded by stopper material, according to which embodiment the sealing element cavity comprises gas but may comprise any deformable material.

According to any embodiment of the invention the sealing element cavity may have any geometric shape in any dimension of the stopper and it may be rectangular, oval, circular, square or any shape in between. The sealing element cavity may have a diameter up to 95% of the stopper body diameter along the deformable sealing element axis. However, the preferred cavity diameter is preferably in the range of 50% to 65% of the along the deformable sealing element axis. The sealing element cavity may have a diameter up to 80% of the stopper body diameter along the stopper longitudinal axis.

In a fourth embodiment the stopper body may be of a material with the ability to expand and retract depending on the surrounding material with which it interacts, thereby achieving the same result as a sealing element cavity according to the invention, but by other means. Certain plastic formulations such as polystyrene combined with e.g. butadiene, or acrylonitrile can be calculated and used to form the stopper body and thereby replace the known elastomeric material opposite the deformable sealing element. By replacing the known elastomeric material in the solid portion of the stopper with a material comprising more significant means of retraction opposite the deformable sealing element the excessive force towards the container inner wall will be reduced. In said embodiment the stopper can be solid opposite the deformable sealing element and may therefore not comprise a sealing element cavity depending on specific force requirements for a given injection system application.

In any embodiment or combination thereof the stopper may have an ability to absorb the excess forces exerted towards the deformable sealing element and further towards the container wall during injection, which a known stopper is unable to do due to the solid portion of elastomeric material in the area opposite the deformable sealing element.

The stopper may be made from any material. In particular, the stopper body is not in contact with the inner wall of the container and the material of the stopper body is generally only required to be inert with respect to any pharmaceutical composition in the injector. The deformable sealing element should likewise be inert with respect to the pharmaceutical composition in the injector.

In one embodiment of the invention the stopper is dyed or pigmented, e.g. the stopper is black, in order to provide contrast between the stopper and the container of the syringe. This contrast will allow more precise dosage when the container comprises indications of the volume. For example, in a container marked with black lines indicating volumes a black stopper can make the indications more easily readable for better control of the volume aspired into or ejected from the injector. However, pigments and dyes may leach from the stopper into the pharmaceutical composition in the injector. This is particularly relevant for injectors prefilled with a pharmaceutical composition since in this case the pharmaceutical composition may be in contact with the stopper for long periods of time. In a preferred embodiment the stopper of the invention does not comprise any pigments or dyes, e.g. the stopper is "transparent". This is particularly preferred when the stopper is used in an injector comprising a pharmaceutical composition, e.g. a prefilled injector, since there is no risk of leakage of dyes or pigments, nor is there an expressed need for above mentioned contrast since the filling of the syringe is done by automated filling equipment at the pharmaceutical company.

In a certain embodiment of the invention the stopper and the deformable sealing element are of the same material, e.g. the stopper body and the deformable sealing element are of the same material, and are manufactured as one component. In one embodiment the stopper and deformable sealing element are manufactured as a single component in any material appropriate for the purpose of a deformable sealing element. By providing the stopper, e.g. the stopper body, and the deformable sealing element, and any optional supporting sealing elements, from the same material, a more cost-effective and simple production is made possible, thereby to a large extent avoiding different process steps e.g. time-consuming assembly. In a preferred embodiment the stopper and or deformable sealing element are made from TPE. A certain compound especially suited is the Evoprene G970 from Mexichem specialty compounds which is a SEBS, and offers the right combination of Shore A hardness combined with a relatively low compression set ratio.

In an embodiment of the invention the stopper is specially dedicated for use with a disposable syringe or a prefilled syringe's piston rod via it's connecting means together with the piston rod's connecting means. According to this embodiment the stopper and piston rod can be manufactured individually followed by the subsequent mounting of the piston rod into the stopper. According to this embodiment an alternative production of the stopper and piston rod is characterised in a dual moulding procedure where the stopper and piston rod are manufactured through a dual moulding sequence ensuring the establishment of the sealing element cavity after the final moulding cycle, whereas the costly assembly step via manual or automated assembly is saved. The said dual or triple moulding principle may be equally relevant for the embodiment comprising a solid material with good expanding and retracting characteristics. In any of the said embodiments including a piston rod these are characterised in that when mounted in the stopper the total width or diameter of the extreme tip of the piston rod which may extend into the sealing element cavity are between 5% and 90% less than the width of the sealing element cavity.

In a sixth embodiment the sealing element cavity is created by an interrupted or uninterrupted circular cylindrical material free area between the sealing element and a solid portion of the stopper towards the centre of the stopper. The material free area defines a vertical cone of a given dimension in the longitudinal axis of the stopper.

In any of the embodiments of the invention the stopper may further comprise a material thickness reduction of the stopper body between the upper and lower sealing elements also known as a resilient frame. This resilient frame is sufficient to provide appropriate resilience. The resilient frame may for example be made from an elastic polymer, e.g. a TPE, or from an elastic metal. In a certain embodiment the material reduction is injection moulded from a TPE, e.g. a styrene block copolymer (SBC), such as SBC selected from the list consisting of hydrogenated SBC or non-hydrogenated SBS or alloys of these. It is especially preferred that the stopper and the resilient frame are injection moulded as a single piece in its final shape from a TPE having a Shore A hardness in the range of 50 to 90, e.g. 70 to 90.

In contradiction to existing stoppers the stopper according to the invention reduces the static force to move the stopper also known as the BLF to move the stopper to significantly lower values by introducing displaced movement of the sealing elements equally dividing the total BLF into smaller increments by stepwise movement of the sealing elements. When the sealing element closest to the container open end called the actuating sealing element has started moving its movement will push the sealing element closest to the container needle end called the passive sealing element, but the present inventor has now surprisingly found that the static friction of the passive sealing element only contributes insignificantly to the force needed to move the stopper and eject liquid from the cylinder so that a smooth movement of the stopper is obtained with the static friction of only the actuating sealing element contributing to the static friction of the stopper.

The maximum BLF felt by the user will thus never be more than the BLF for one sealing element. The following values exemplify the BLF force obtained in an embodiment of the invention: the BLF of the actuating sealing element 7 N reduced to a mean glide force 4 N increased to a BLF of the passive sealing element 7 N reduced to mean glide force 4 N for injection completion, equivalent to approximately 50% of the BLF of a traditional stopper of about 14 N. The stopper according to the invention is hence able to reduce the BLF to half value or lower compared to any known stopper.

The resilient frame comprises a thickness dimension which will ensure differential movement of the stopper sealing elements thereby reducing the BLF. Unlike traditional stoppers which move all sealing elements simultaneously, the resilient frame ensures that the sealing element closest to the container opening which is first activated by the plunger rod will move before movement of the sealing element closest to the container needle end. By differential movement the total BLF is significantly reduced achieving a significantly improved gliding performance ultimately increasing injection stability, user friendliness and comfort for the patient, where abrupt and sudden movement of the plunger rod can result in highly unpleasant experience for the patient.

The dimension of the resilient frame may vary in length and thickness along the longitudinal and the horizontal axis of the stopper. The resilient frame may further vary in thickness dimension for one given stopper.

The deformable sealing element is made from a material of an appropriate hardness and elasticity to ensure that the annular gap between the stopper and the inner wall of the container is sealed. Any TPE material may be chosen for the deformable sealing element. In a preferred embodiment the stopper and the deformable sealing element of the invention is made in one component by injection moulding from an appropriate thermoplastic polymer, such as Evoprene manufactured by Mexichem, which is a chemically inert SEBS formulation. The stopper is preferably injection moulded and thereby the deformable sealing element can be made with lower tolerances than afforded by traditional rubber stoppers manufactured by traditional vulcanisation technologies. Appropriate stopper materials comprise elastomers, such as halobutyl rubber, e.g. chlorobutyl, bromobutyl, natural rubber, synthetic rubber (polyisoprene rubber, butyl rubber), silicone rubber, thermoplastic elastomers as TPE and the like, which may be defined with respect to e.g. the Shore durometer, which indicates the elasticity of the elastomeric material and measures the hardness of the elastomeric material, where the higher the durometer, the harder the compound. For example, in one embodiment of the invention the deformable sealing element or the stopper and the deformable sealing element has a Shore A hardness in the range of about 30 to about 90, preferably 60 to 80, more preferred 70 to 76. The terms "Shore hardness" and "Shore durometer" may be used interchangeably. In general, the deformable sealing element will be homogeneous and composed of the same material throughout the volume of the deformable sealing element, which material has a Shore A hardness in the given ranges. By using a material with a Shore A hardness in the above mentioned range, a relatively hard elastomeric material is provided. The harder material compared to known stoppers is especially advantageous with respect to reducing the abutting interface with the container inner wall while maintaining adequate container closure at the same time, since the harder material reduces the normal tendency of butyl rubber and other known materials who's softer material have a significant expansion along the barrel inner wall when inserted thereby obtaining a substantial abutting interface and hence a substantial adhesion area increasing forces between the deformable sealing element and the container inner wall.

The stopper may have one or more deformable sealing elements as defined above although the stopper may also have additional sealing elements with other shapes and functions. For example, the stopper may have a supporting sealing element capable of guiding or controlling the orientation of the stopper in the cylinder. Further it may have supporting elements without sealing capability but with physical ability to support the correct positioning of the stopper inside the container.

Tests have shown that a deformable sealing element having a diameter of 1.5% more than the container inner diameter is sufficient to obtain full container closure for a given material, although most stopper deformable sealing elements have a diameter which is at least 3% larger than the inner diameter of the container. Ultimately the hardness of the sealing element raw material and or the design has influence on the choice of deformable sealing element diameter.

Further tests have shown that two stoppers with identical raw material, deformable sealing element profiles and diameters will differ significantly in static and dynamic forces depending on whether they are solid or comprise a sealing element cavity behind the deformable sealing element.

Other tests confirm that a cavity according to the invention may reduce the BLF with 35.26% for Tween solution liquid and 56% for WFI liquid. Additionally, the cavity according to the invention will reduce the dynamic force, also known as the "mean gliding force", of the stopper with 73.68% for Tween solution liquid and 62.5% for WFI liquid.

The stopper is for an injector, and in another aspect the invention relates to an injector with the stopper. The deformable sealing elements seals an annular gap between the inner wall and the stopper body when the stopper is inserted into the cylinder. Any embodiment of the stopper may be used in an injector of the invention. The injector comprises a cylinder, and in the context of the invention a "cylinder" is any kind of tube or the like allowing the stopper to be moved from one position in the cylinder to another. The cylinder has an "actuating end" and "outlet end" opposite each other. The actuating end of the cylinder allows access to the stopper for moving it, i.e. "actuating" the stopper via the actuating surface, in the cylinder. The outlet end of the cylinder comprises an outlet for a fluid contained in the cylinder.

The outer diameter of the deformable sealing element is typically 1.5% to 10% larger than the inner diameter of the cylinder, e.g. 2% to 5% larger. When the injector of the invention is used with a stopper having a deformable sealing element with an outer diameter in the range of 1.5% to 10% larger than the inner diameter of the cylinder, and when the deformable sealing element has a Shore A hardness in the range of 30 to 90, e.g. in the range of 50 to 90, or 70 to 90, the injector does not require an external lubricant. Thus, in an embodiment of the invention, the injector does not comprise an external lubricant.

The cylinder may be made from any relevant material, and typical materials comprise polymeric materials, such as cyclic olefin copolymer (COC), e.g. TOPAS polymers (supplied by TOPAS Advanced Polymers GmbH), cyclic olefin polymer (COP), e.g. Zeonor, or polystyrene, or glasses, e.g. borosilicate glasses. Borosilicate glass generally has superior barrier characteristics compared to plastics. COC polymers are advantageous due to their excellent barrier characteristics and thus accommodate the need for long-term storage of pharmaceutical agents. In another embodiment the cylinder is made from glass, e.g. borosilicate glass. It is also contemplated that the cylinder may be made from a metal or it may comprise any combination of polymeric materials, glasses or metals. The cross-sectional shape of the cylinder is not limited although it is preferred that the cylinder has a round cross-section. It is also contemplated that the cross-section may be oval, elliptical, polygonal, etc. When the cylinder has a round cross-section the diameter, e.g. the inner diameter, may have any value conventionally used with syringes. For example, in a preferred embodiment the cylinder has an inner diameter in the range of 2 mm to 12 mm, such as 4.65 mm, 6.35 mm, 8.65 mm or 11.85 mm, although it may have larger values according to the invention.

When the deformable sealing element is a TPE with a Shore A hardness in the range of 30 to 90 the effect of the cavity is on the reduction of the BLF is so pronounced that the stopper can be used without external lubrication. In this context, external lubrication includes silicone oils, silicone baked on the inner surface of the cylinder of an injector, perfluoro polymers on either the surface of the stopper or the inner surface of the cylinder of an injector. The present invention has, in particular, observed that an injector with a stopper of the invention with the deformable sealing element made from the TPE can be used with a pharmaceutical composition that does not comprise lubricating ingredients.

In an embodiment, the stopper comprises a deformable sealing element made from a TPE, and the injector does not comprise a lubricant, in particular the injector does not comprise a silicone lubricant. Lubricants, e.g. silicone lubricants, are not inert with respect to certain pharmaceutical compounds, e.g. pharmaceutical compounds based on protein molecules, such as vaccines, and lubricants should be avoided for long term storage of injectors prefilled with a pharmaceutical compound. Therefore, this embodiment advantageously allows long term storage of an injector of the invention prefilled with a pharmaceutical compound, e.g.

a protein based pharmaceutical compound, without detrimental effects on the pharmaceutical compound. When the deformable sealing elements that contacts the inner surface of the cylinder, is made from a TPE having a Shore A hardness in the range of 30 to 90, the stick-in effect is avoided even when no lubricant, e.g. a silicone lubricant, is present, and in particular when the compression set at ambient temperature is in the range of 15% to 40%. Thus, any embodiment where the deformable sealing element is made from a TPE having a Shore A hardness in the range of 30 to 90 and where no lubricant is present is especially suited for long term storage, since no stick-in effect occurs, long term sealing is provided and negative effects on the pharmaceutical from a lubricant are avoided while still retaining a smooth end user experience due to the reduction in the BLF afforded by the stopper of the invention. The effect is observed for injectors having polymeric as well as glass cylinders. These effects are particularly relevant when the stopper comprises an actuating stopper element and an outlet stopper element linked together by a resilient frame, and thus in one embodiment the injector comprises a stopper with an actuating stopper element and an outlet stopper element linked together by a resilient frame as defined above.

Lubrication free interaction is especially suitable for injectors with glass cylinders, an in an embodiment the injector comprises a glass cylinder, and the stopper has a deformable sealing element made from a TPE with a Shore A hardness in the range of 30 to 90, and the injector does not comprise lubrication, e.g. external lubrication compared to the stopper. In a specific embodiment, the injector comprises a glass cylinder, e.g. a borosilicate glass cylinder, and the injector comprises a stopper with an actuating stopper element and an outlet stopper element linked together by a resilient frame as defined above, and the injector does not have a lubricant.

In general, glass cylinders which have inner diameter tolerances too wide to interact with traditional pistons and omit lubrication at the same time due to too high BLF values for the traditional piston. At low diameter values the BLF will be too high and at high diameter values the container closure integrity (CCI) will be compromised with traditional pistons. In contrast the stopper employed in the present invention is capable of compensating for the wide tolerances due to its displaced movement of the deformable sealing elements which allows for a larger piston diameter while still keeping the BLF within acceptable values, at the same time enabling omittance of traditional lubrication.

In an embodiment the cylinder is made from glass, e.g. borosilicate glass, and the injector does not comprise a lubricant, especially a silicone based lubricant. The combination of the efficient sealing obtained and the reduced BLF is especially advantageous for long term storage of a prefilled injector, since the stick-in effect does not occur, and moreover detrimental effects of lubricants on the pharmaceutical composition, e.g. a protein based pharmaceutical composition, are avoided. The invention can be said to provide an injector for long term storage of a pharmaceutical composition, which does not suffer from stick-in effects.

The injector may be any kind of injector employed to deliver a pharmaceutical composition to a subject through the skin of the subject. For example, the injector may be a syringe, which is fitted with a hypodermic needle to inject a pharmaceutical composition, e.g. via subcutaneous (SC), intramuscular (IM), intra-dermal (ID), or intravenous (IV) delivery or another type of delivery.

The injector may comprise, e.g. at the outlet end, a fitting for attaching or mounting a hypodermic needle. The cylinder may thus have a tapered outlet, e.g. a tubular outlet, from the cylinder providing an engagement device for engaging a complementary engagement device of a hypodermic needle, e.g. the engagement device and the complementary engagement device may comprise a male-female interaction, with the tubular outlet optionally comprising an external thread, e.g. a helical external thread, and the hypodermic needle optionally comprising a complementary internal thread, e.g. a helical internal thread. A hypodermic needle may be fitted to allow simple removal, and replacement, of the hypodermic needle, or the hypodermic needle may be mounted permanently on the injector. In particular, the hypodermic needle may be mounted on the injector so that its removal requires the destruction of the injector thereby preventing reuse, which in the context of the invention is considered "permanent". It is preferred that the injector comprises a hypodermic needle attached, e.g. permanently attached, to the outlet of the cylinder.

In an embodiment of the invention the injector, preferably prefilled, is a syringe with a hypodermic needle. The syringe may have a hypodermic needle mounted, e.g. permanently mounted, on a tubular outlet or an outlet of another shape. When the injector is prefilled, in particular when it also comprises a needle cap for use as a piston rod, there may be a clearance between the actuating end of the cylinder and the actuating surface of the stopper. The clearance ensures stability of a piston rod when this is inserted in the cylinder, which results in a safer and easier operation of the injector. The clearance, e.g. measured in units of length, may be any value relevant for the size, e.g. volume, of injector and the dose of pharmaceutical composition in the injector. Typical values for the clearance are between about 2 mm to about 20 mm. However, the clearance may be in excess of 20 mm in cases where the actual volume of the injectable volume is considerably less than the cylinder usable volume, e.g. for ophthalmic injections where the injectable volume is only between 0.01 ml and 0.2 ml, e.g. 0.05 ml, although the injector body and hence the cylinder is considerably larger and especially longer in order for the user to be able to handle and control the injector.

The injector of the invention is preferably a prefilled injector. Tests have shown that the stopper according to the invention has different static and dynamic forces when comparing forces from testing identical stoppers with identical cylinders depending on the contents of these. With identical components involved tests show that the BLF and gliding force are reduced when testing cylinders filled with WFI (Water for Injection) or Tween solution (Tween80 solvent). Conversely BLF and gliding force are higher when testing empty cylinders. This result indicates that the stopper and sealing elements according to the invention has a lubricating effect during interaction with a liquid of the type mentioned so that the injector is especially suited for an injector prefilled with a pharmaceutical composition, in particular a pharmaceutical composition that does not comprise any lubricating additives. There is reason to believe that this interaction between the outlet end sealing element is further improved with a pharmaceutical injectable which normally comprise vehicles in the form of plasticisers and or additives in the form of oils which will reduce friction forces even further.

The features of the injectors of any aspects of the invention may be combined freely and any advantage obtained for a specific feature is available to either aspect by incorporated the respective feature in the injector.

BRIEF DESCRIPTION OF THE FIGURES

In the following the invention will be explained in greater detail with the aid of examples and with reference to the schematic drawings, in which.

It should be understood that combinations of the features in the various embodiments are also contemplated, and that the various features, details and embodiments may be combined into other embodiments.

Reference to the figures serves to explain the invention and should not be construed as limiting the features to the specific embodiments as depicted.

DETAILED DESCRIPTION OF THE INVENTION

The present invention relates to stoppers for injectors for delivery of a pharmaceutical composition and to injectors. The present invention will now be described in greater detail with reference to the appended drawings. Certain figures are depicted as "cross-sectional views" of the injectors of the invention, where the injector in the "cross-sectional view" is depicted at an angle of 90° compared to the injector otherwise depicted. Certain figures depict side views of injectors of the invention. These side views do not depict the outlet of the injectors but it is to be understood that the injector of the invention will have an outlet, e.g. fitted with a hypodermic needle.

Figure 1:
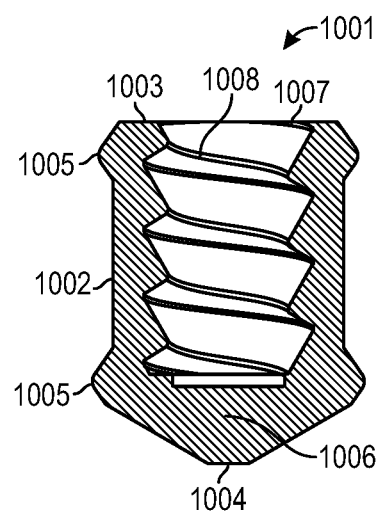
FIG. 1 shows a stopper of the prior art.

FIG. 1 shows an example of a stopper 1001 of the prior art. The stopper 1001 has a piston body 1002 with and an actuating end 1003 and an outlet end 1004, and the actuating end 1003 comprises a tubular section 1007 having an internal helical thread 1008. The stopper 1001 comprises two deformable sealing elements 1005. The stopper 1001 has a solid section 1006. The stopper 1001 thus exerts substantial force from the solid elastomeric material 1006 via the deformable sealing element 1005 and towards the container inner wall (not shown) dictating the use of lubrication means for satisfactory injection functionality causing significant disadvantages.

Figure 2:
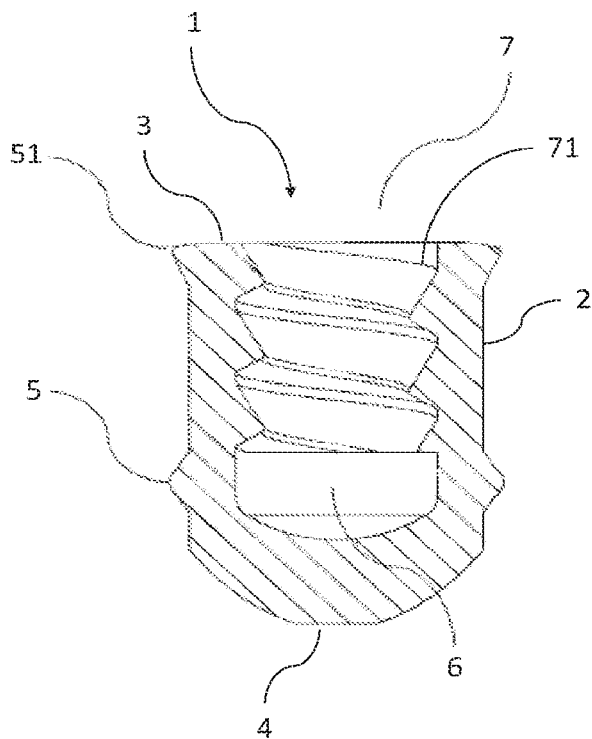
FIG. 2 shows a cross-sectional view of a stopper of the invention.
Figure 3:
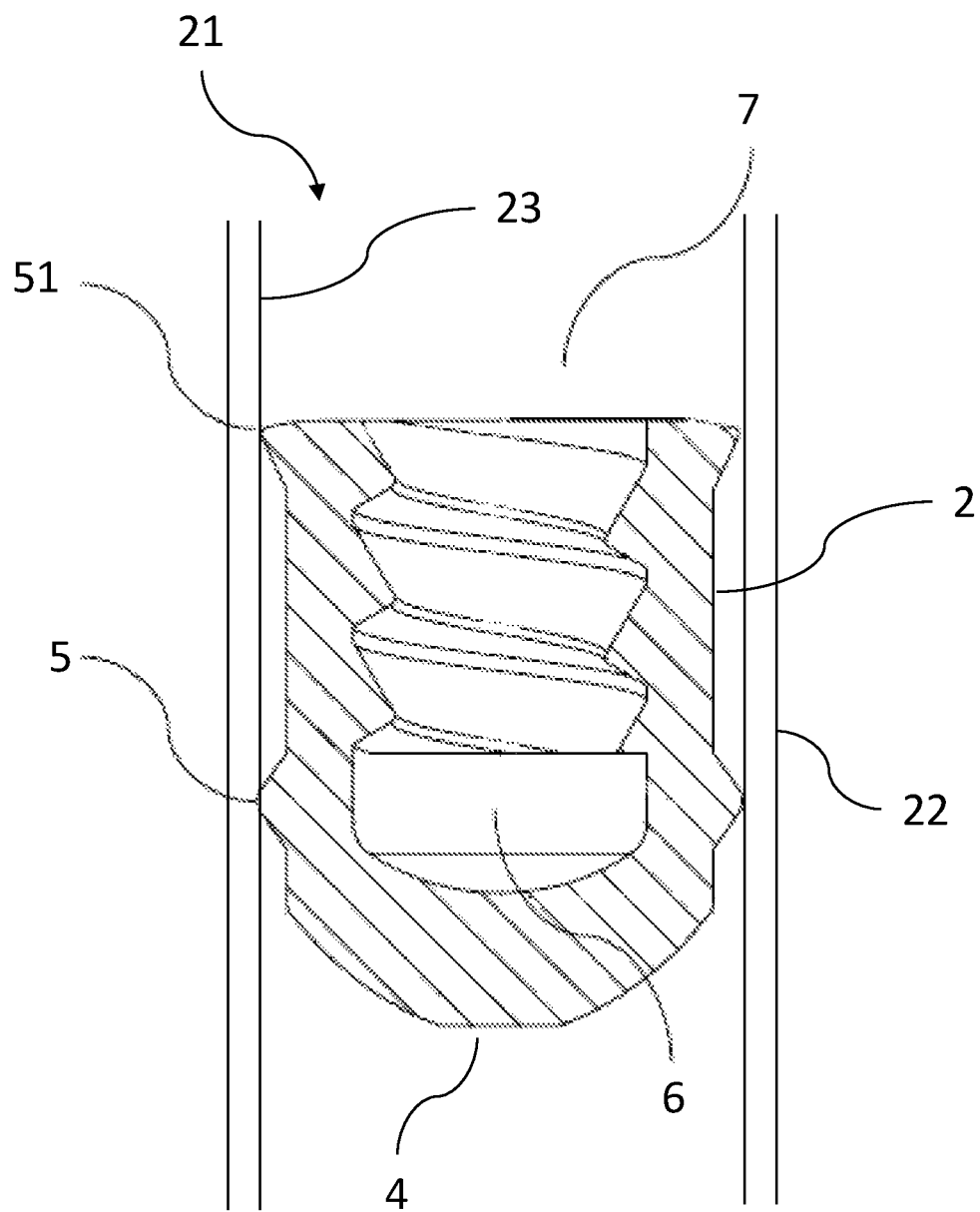
FIG. 3 shows a cross-sectional view of an injector of the invention.
Figure 4:
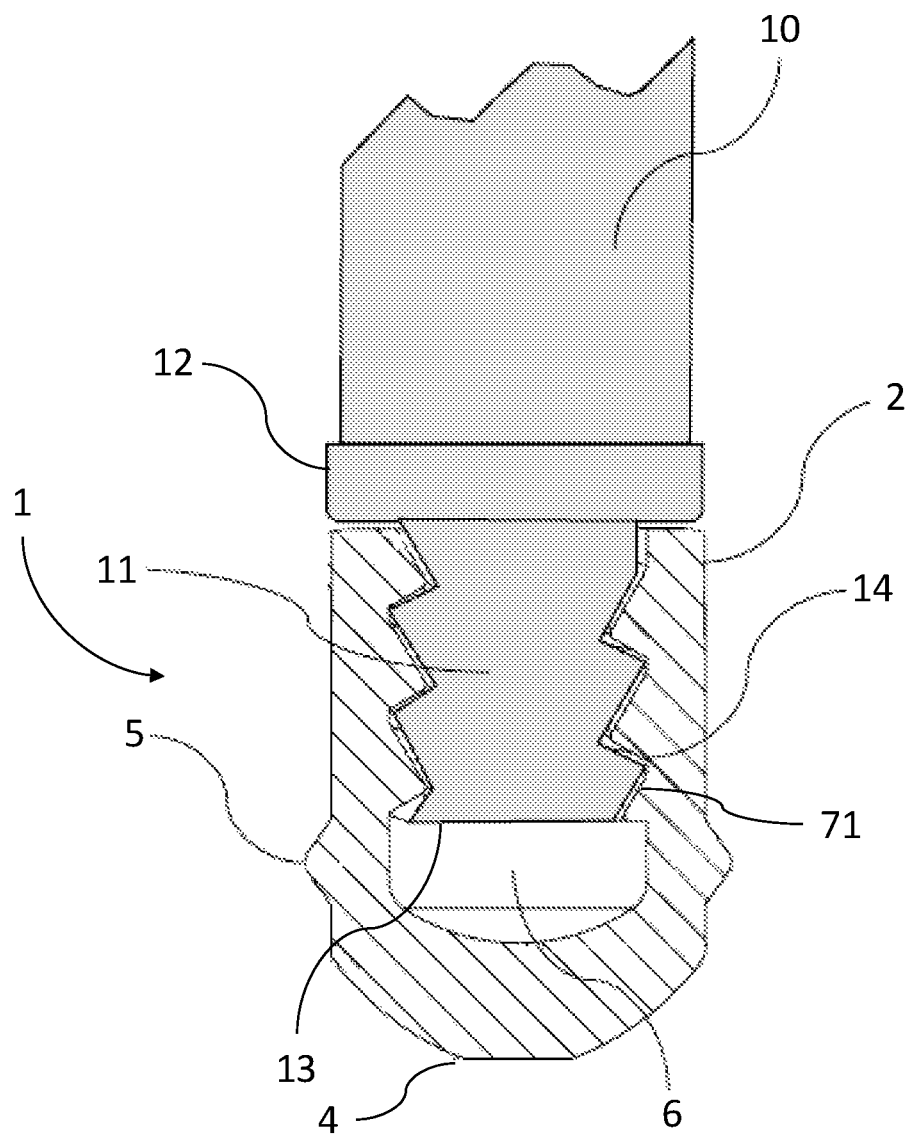
FIG. 4 shows a cross-sectional view of a stopper of the invention with a piston rod.
Figure 5:
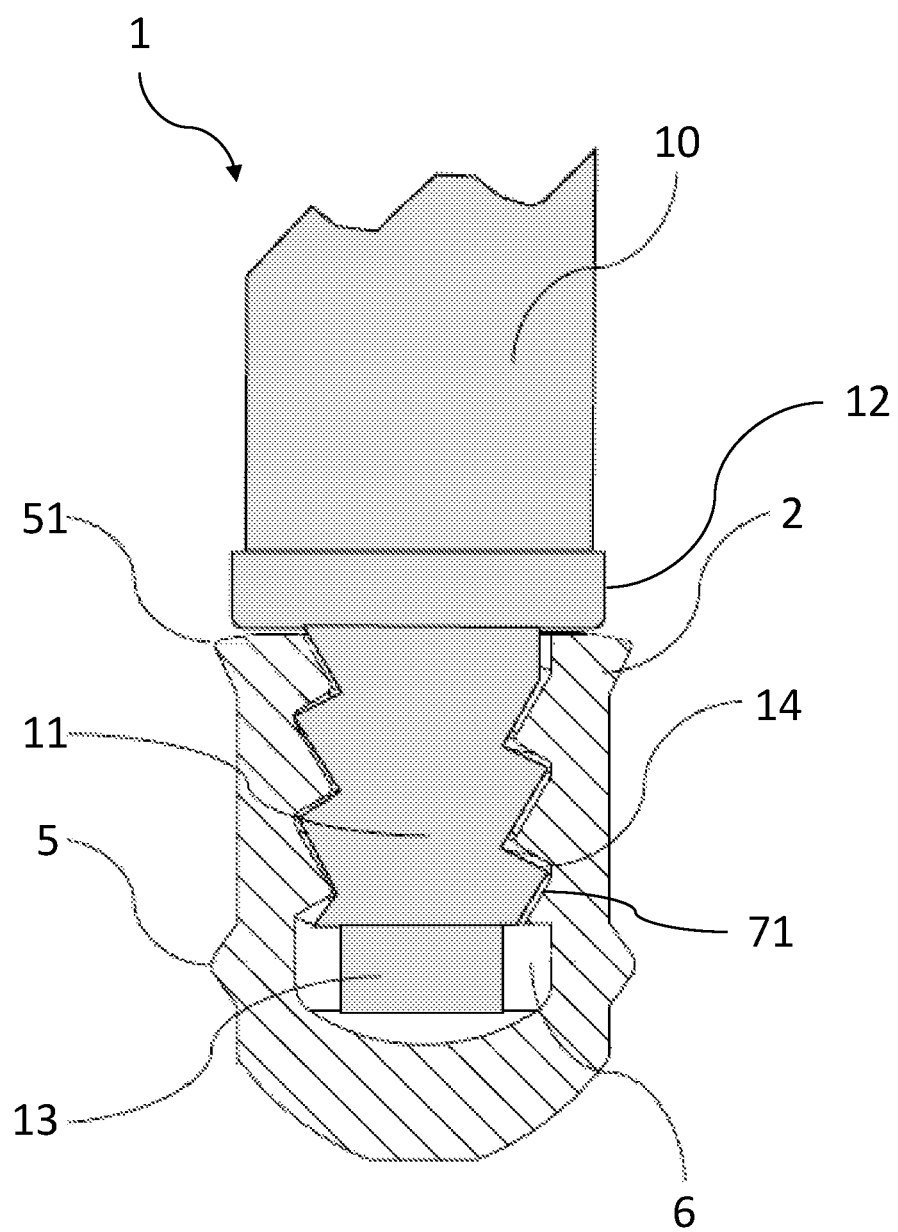
FIG. 5 shows a cross-sectional view of a stopper of the invention with a piston rod.

FIG. 2 shows an embodiment of a stopper 1 of the invention, and in FIG. 3 the stopper 1 has been inserted into an injector 21 of the invention. The depicted stoppers 1 are injection moulded as single pieces from a thermoplastic elastomer (TPE). In FIG. 4 and FIG. 5 the stopper 1 is depicted with different embodiments of a piston rod 10. The stopper 1 has a stopper body 2 with an actuating surface 3 opposite an outlet surface 4, and an axial length between the actuating surface 3 and the outlet surface 4. The stopper body 2 has a transverse diameter, and the stopper body 2 defines an access diameter. At an axial location from the actuating surface 3 the stopper 1 comprising a deformable sealing element 5 surrounding the stopper body 2 and having an outer diameter, which is larger than the transverse diameter. The deformable sealing element 5 has an axial extension in the range of 5% and 95% of the axial length of the stopper body 2. When inserted into a cylinder 22 of a syringe 21 the deformable sealing element 5 abuts the inner wall 23 of the cylinder 22 so that the deformable sealing element 5 seals an annular gap between the inner wall 23 and the stopper body 2. The stopper 1 is depicted with a supporting sealing element 51, which also abuts the inner wall 23. When a supporting sealing element 51 is present it will typically have a smaller diameter than the diameter of the deformable sealing element 5, which has a lateral extension, a diameter, in the depicted embodiment, larger than the access diameter of the stopper body 2. The supporting sealing element 51 can prevent tilting of the stopper 1 when the stopper 1 is mounted in the cylinder 22. The deformable sealing element 5 is made from a TPE; in the embodiment shown, the TPE is a non-lubricated Evoprene G970 (Mexichem Specialty Compounds).

A tubular section 7 extends from the actuating surface 3, and the tubular section 7 has in internal helical thread 71 representing an engagement device for engaging a complementary engagement device of the engagement section 11 of the piston rod 10. Thus, the cavity 6 is formed in the interface between the terminal site 13 of the engagement section 11 of the piston rod 10 and the deformable sealing element 5 when the piston rod 10 is inserted into the tubular section 7. Specifically, the complementary engagement device is an external helical thread 14. The internal helical thread 71 defines has a minimum diameter and a maximum diameter defined by the helix. The minimum diameter of the helix will, in this embodiment, be the access diameter defined by the stopper body 2.

The piston rod 10 will normally be made from a hard polymeric material. The piston rods 10, as depicted, have a ridge 12, which has a larger diameter than the largest diameter of the helix of the internal helical thread 71, but smaller than the inner diameter of the cylinder 22. Thereby, the ridge 12 defines how deep into the tubular section 7 the engagement section 11 of the piston rod 10 can be inserted. When the engagement section 11 of the piston rod 10 has been fully inserted into the tubular section 7, i.e. in the embodiments shown the engagement section 11 is screwed into the tubular section 7, a cavity 6 is formed between the terminal site 13 of the piston rod 10. The cavity 6 may thus be a cylindrical cavity 6 as shown in FIG. 4 or a toroidal cavity 6 as shown in FIG. 5. In both cases the cavity 6 has a lateral extension, e.g. a diameter, larger than the access diameter of the stopper body 2.

Figure 6:
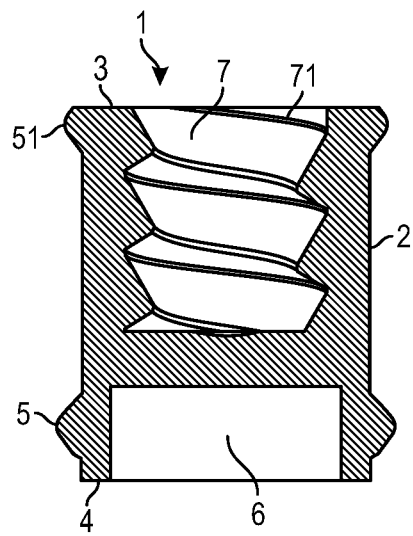
FIG. 6 shows a cross-sectional view of a stopper of the invention.

FIG. 6 shows an embodiment of the stopper 1, where the stopper 1 has a cavity 6 at the axial location of a deformable sealing element 5 closest to the outlet surface 4 of the stopper 1, which cavity 6 is open to the outlet surface 4.

Figure 7:
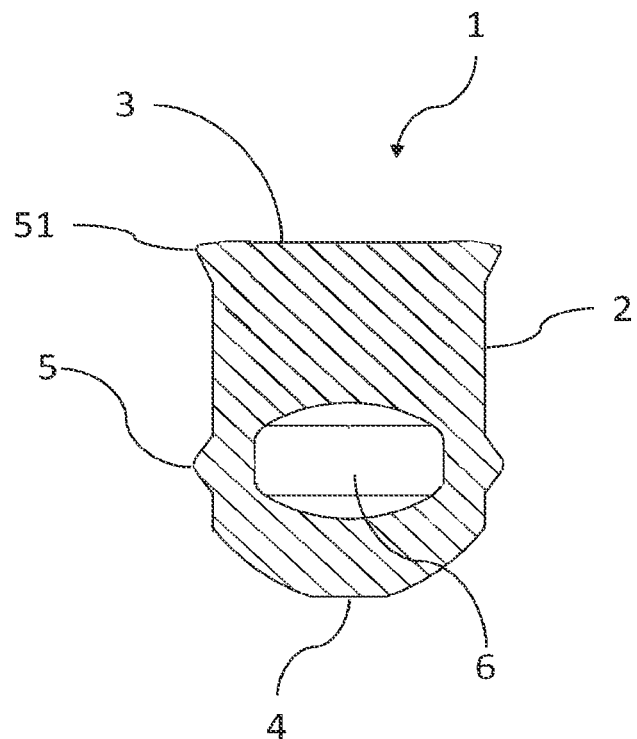
FIG. 7 shows a cross-sectional view of a stopper of the invention.

FIG. 7 shows an embodiment of the stopper 1, where the stopper 1 has a cavity 6, which is enclosed in the TPE of the stopper. The stopper 1 may for example be injection moulded as two pieces, where one piece is the stopper body 2 having an open cavity 6 as depicted in FIG. 6 an another piece is a tip that can be attached to the stopper body 2 so that the cavity 6 is enclosed between the material of the tip and the stopper body 2 after welding. The stopper 1 in FIG. 7 does not have a tubular section 7 but a stopper body 2 having a tubular section 7 can also be prepared with an enclosed cavity 6 as shown in FIG. 7.

Figure 8:
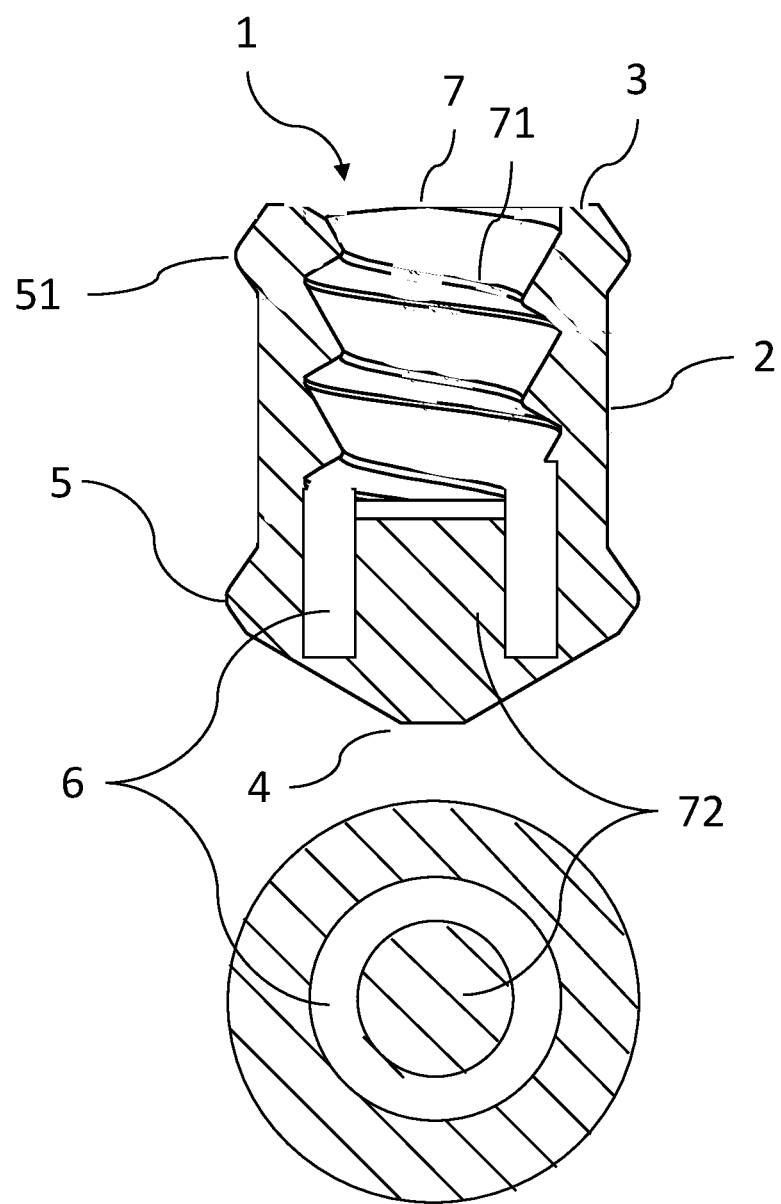
FIG. 8 shows a cross-sectional view and a top view of a stopper of the invention.
Figure 9:
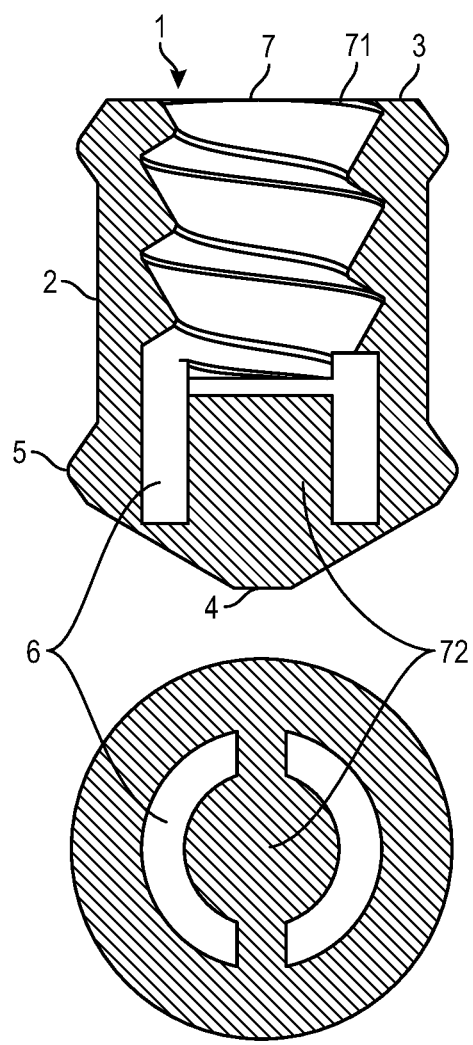
FIG. 9 shows a cross-sectional view and a top view of a stopper of the invention.
Figure 10:
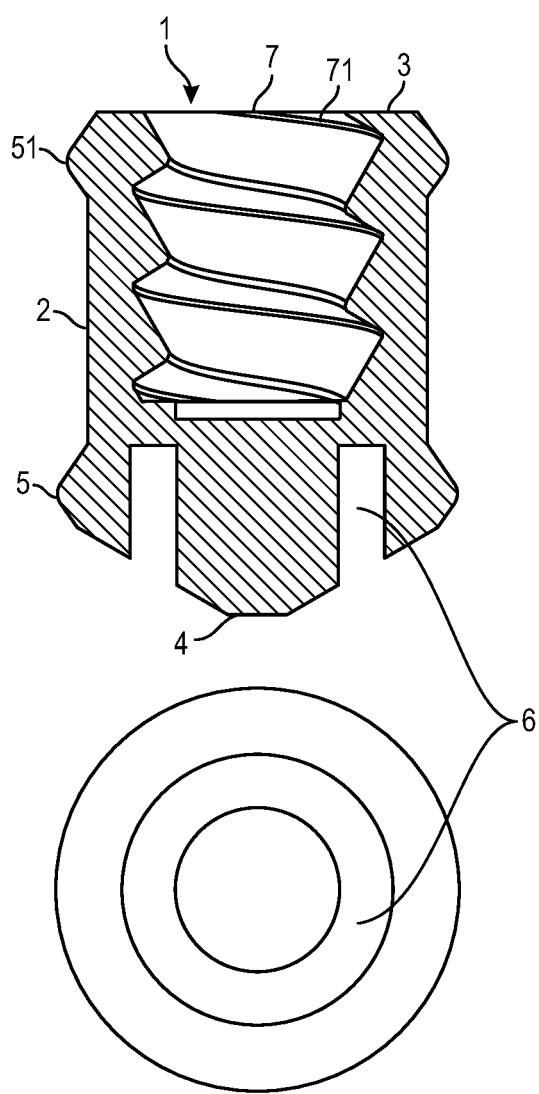
FIG. 10 shows a cross-sectional view and a top view of a stopper of the invention.

FIG. 8, FIG. 9 and FIG. 10 show embodiments of the stopper 1, where the cavity 6 has a toroidal shape. In the top panels, the stoppers 1 are depicted in a cross-sectional view and in the bottom panels, the stoppers 1 are depicted in a top view. In all three embodiments shown, the stoppers 1 are preferably prepared by injection moulding as single pieces of a TPE. In FIG. 8 and FIG. 9 the tubular section 7 has a protrusion 72 at the bottom of the tubular section 7, which protrusion 72 extends into the tubular section 7. Thereby, toroidal cavities 6 will be formed when the piston rod (now shown in FIG. 8 and FIG. 9) is inserted into the tubular section 7. In FIG. 9 the protrusion 72 is shaped to form a toroidal cavity 7 shaped to form two subcavities so that the cavity 7 has the shape of an interrupted cylindrical shell. In FIG. 10 the tubular section 7 is separated from the cavity 6, which is instead formed to extend from the outlet surface 4 and into the stopper body 2.

Figure 11A:
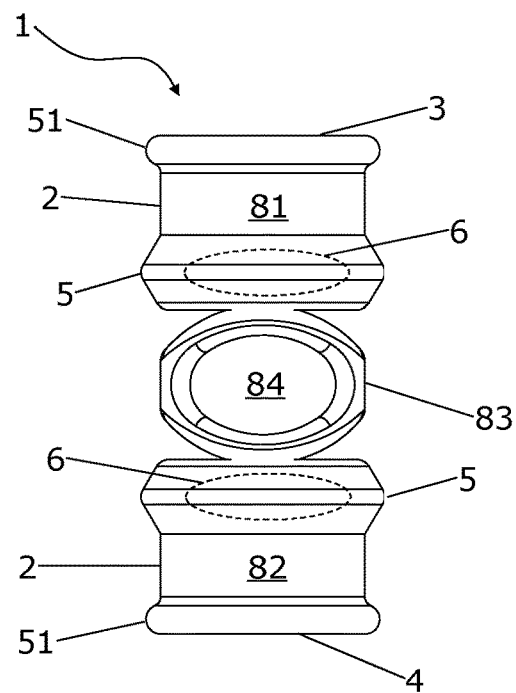
FIG. 11 shows an embodiment of a stopper of the invention having a resilient frame.
Figure 11B:
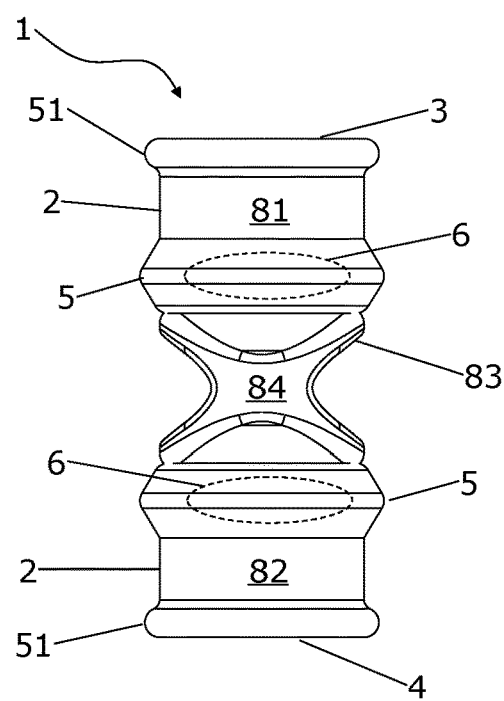
Figure 12A:
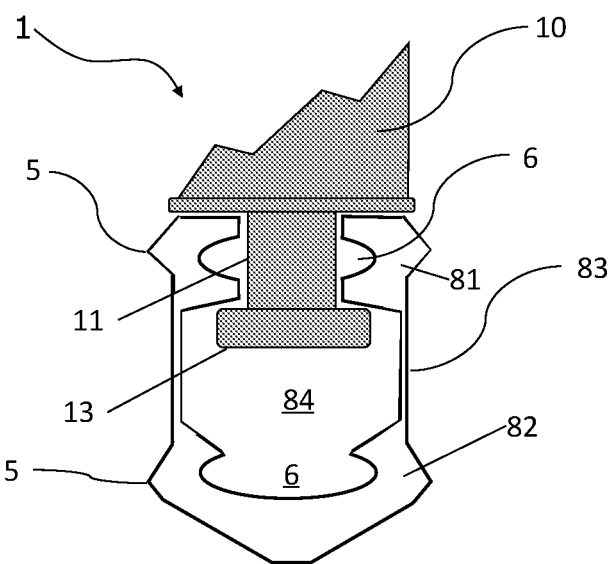
FIG. 12 shows an embodiment of a stopper of the invention having a resilient frame.
Figure 12B:
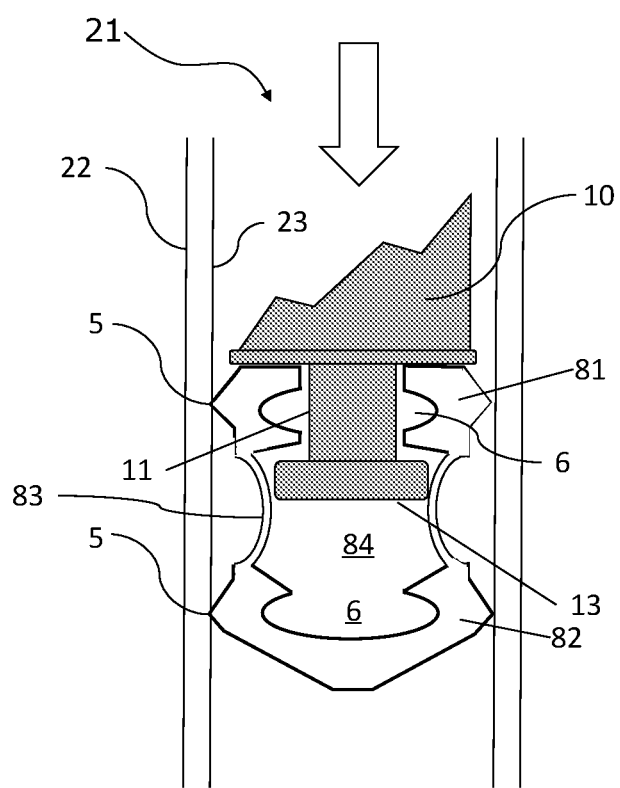
Figure 13A:
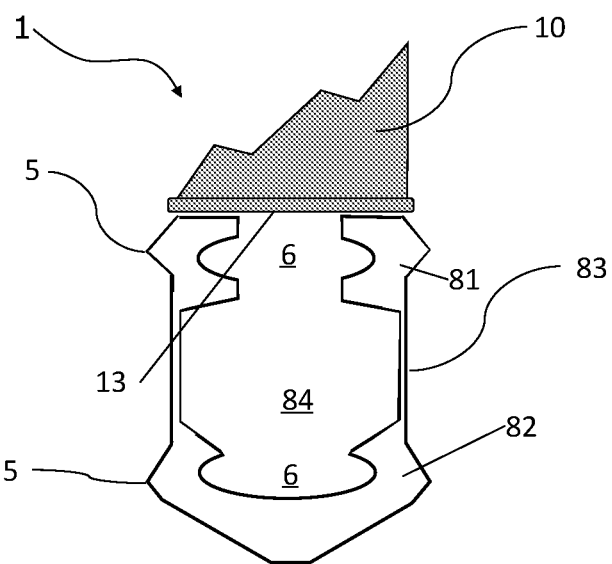
FIG. 13 shows an embodiment of a stopper of the invention having a resilient frame.
Figure 13B:
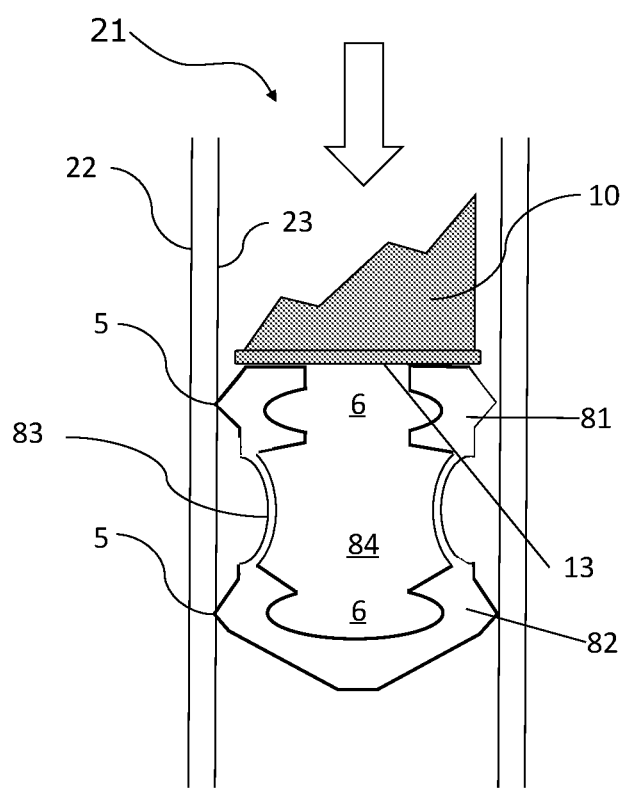

FIG. 11, FIG. 12 and FIG. 13 show embodiments of the stopper 1 having a resilient frame 83. These stoppers are preferably made as single pieces by injection moulding of a TPE. In FIG. 11 the stopper 1 is shown at different angles at 90° relative to each other in the a and b panels, respectively. In FIG. 12 and FIG. 13 panels a show the stoppers 1 and in panels b the stoppers 1 are inserted into cylinders 22 of injectors 21. Thus, the stopper 1 has an actuating stopper element 81 and an outlet stopper element 82, which are linked together by the resilient frame 83. The actuating stopper element 81 and the outlet stopper element 82 abut the inner wall 23 of the cylinder 22 and seal a gap between the inner wall 23 of the cylinder 22 and the stopper body 2 thereby creating a compressible section 84 between the actuating stopper element 81 and the outlet stopper element 82. The embodiments depicted have cavities 6 at both deformable sealing elements 6. In FIG. 12 and FIG. 13 panels b show how the resilient frame 83, which has a cylindrical shape, can deform upon application of a force as depicted with an arrow. The arrows thus represent the force occurring when the piston rod 10 is pushed toward the outlet end of the cylinder 22. The stopper 1 in FIG. 12 has a piston rod 10 with an engagement section 11 having a terminal site 13 with a larger diameter than the tubular section 7 so that the terminal site 13 functions as a barb that can pull the stopper 1 back and thereby fill the cylinder 22 of the injector 21.

Figure 14:
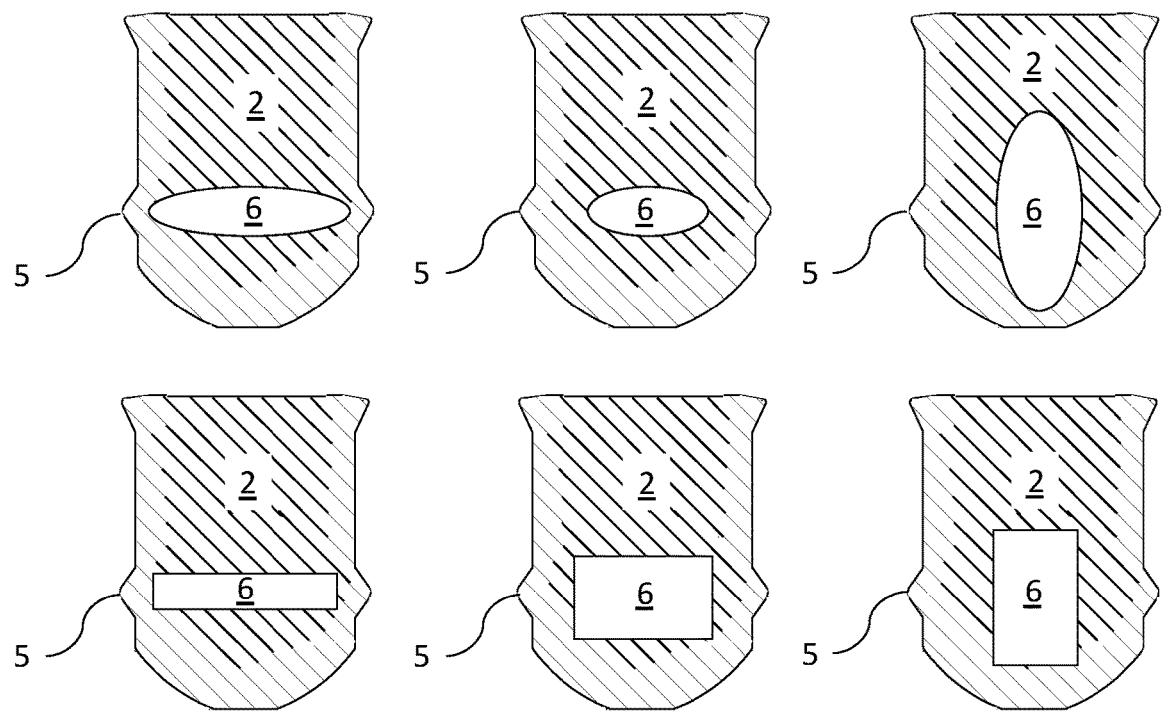
FIG. 14 shows several embodiments of stoppers of the invention.
Figure 15:
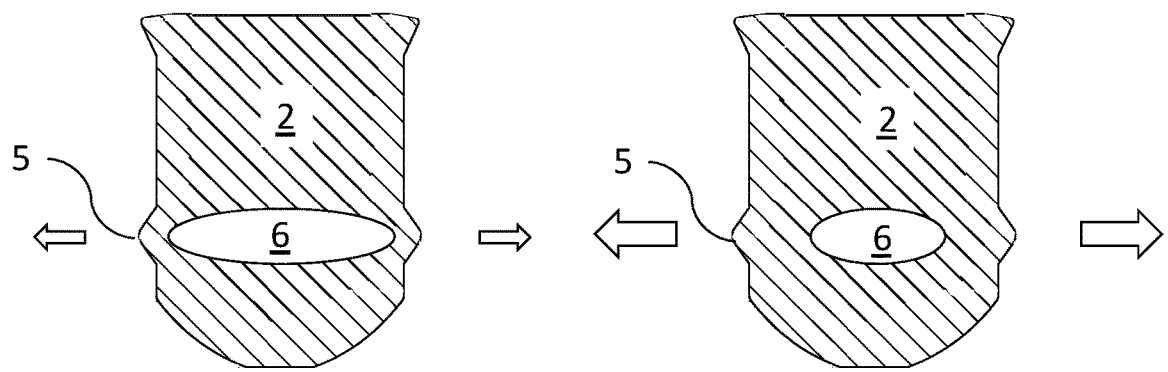
FIG. 15 shows embodiments of stoppers of the invention.

FIG. 14 shows several embodiments of the stopper 1 having a cavity 6 enclosed in the stopper body 2, and in FIG. 15 similar stoppers 1 are shown with cavities 6 having different diameters, in the left and right panels, respectively, where arrows indicate the force exerted on the inner wall 23 of the cylinder 22 via the deformable sealing element 5. Thus, the smaller the diameter of the cavity 6 the larger the force on the inner wall 23 and thereby the higher the break loose force (BLF). Therefore, the lateral extension of the cavity 6 should be at least 50% of the outer diameter of the deformable sealing element 5. If the lateral extension of the cavity 6 is below 50% of the outer diameter of the deformable sealing element 5 a sufficiently low BLF may not be possible to avoid lubrication of the stopper.

Figure 16:
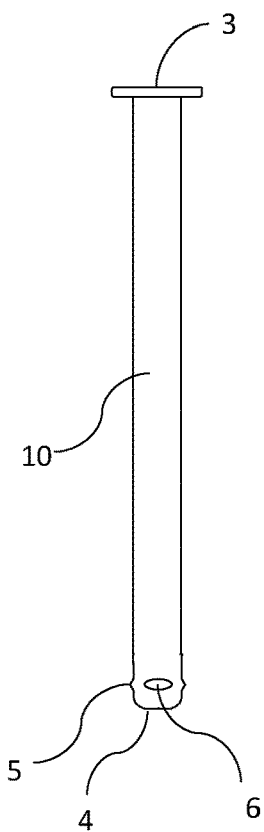
FIG. 16 shows an embodiment of a piston rod of the invention

FIG. 16 shows how the cavity 6 may be integrated in a piston rod 10. Thus for example, the piston rod 10 may have a cylindrical section with an integrated stopper 1. Alternatively, the piston rod 10 may have a cylindrical section corresponding to the engagement section 11, which is surrounded by an O-ring made of a TPE the O-ring having a recess thereby providing the cavity 6 when mounted on the piston rod 10. In yet a further embodiment, the piston rod 10 may have a cylindrical section corresponding to the engagement section 11, which is surrounded by a sleeve made from a TPE, the sleeve comprising one, two or more deformable sealing elements 5 with cavities 6 formed between the inner surface of the sleeve and the outer surface of the engagement section part of the piston rod 10.

Figure 17:
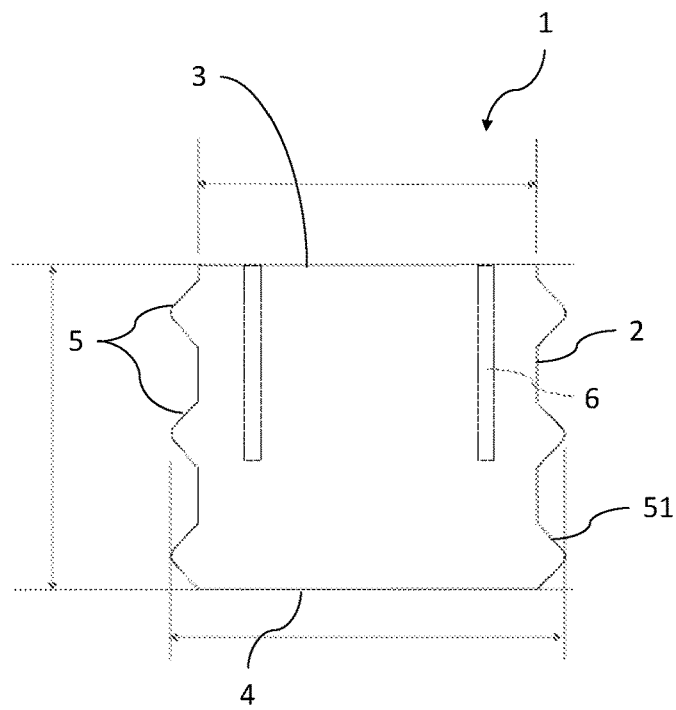
FIG. 17 shows an embodiment of a stopper of the invention.

A further embodiment of the stopper 1 of the invention is shown in FIG. 17. In this embodiment, the stopper has two deformable sealing elements 5, which share a toroidal cavity 6 extending from the actuating surface 3 of the stopper 1. Thus, the cavity 6 extends between the axial locations of the deformable sealing elements 5. The stopper 1 has a supporting deformable sealing element 51.

EXAMPLES

Example 1

The stopper depicted in FIG. 2 was prepared by injection moulding from the TPE material Evoprene G970 (Mexichem Specialty Compounds). The stopper had two deformable sealing elements. The stopper was mounted in 1.0 ml non-lubricated borosilicate glass cylinder of 6.35 mm inner diameter with 27 G staked needle and provided to the test facility as pre-filled glass injectors with the integrated needle and stored at 23° C., 50% relative humidity (RH) until testing began. The tests involved analysis of the BLF and the glide force in Water for Injection (WFI) and an aqueous solution of Tween. Testing was based on ISO 7886-3:2005 Annex B Sterile hypodermic injectors for single use—Part 3: Autodisable injectors for fixed-dose immunisation, Test method for forces required to operate plunger. The specific conditions involved emptying the injectors with measurement of forces during the initial 5 mm at a test rate of 100 mm/min in an Instron mechanical testing machine equipped with 100 N load cell. The test results are shown in Table 2.

TABLE 2

BLF test results for 1 ml injector, 2-deformable sealing elements stopper.

| Test conditions 23° C., 50% RH | Number of replicates | Average BLF (N) | Glide force, N 2-30 mm |
|---|---|---|---|
| WFI | 4 | 10 (1) | 5.2 (1.9) |
| Tween solution | 4 | 9.2 (0.7) | 3.7 (0.7) |

For comparison stoppers were prepared having only a single deformable sealing element and the tests were repeated. The results are shown in Table 3.

TABLE 3

BLF test results for 1 ml injector,
1-deformable sealing element stopper.

| Test conditions 23° C., 50% RH | Number of replicates | Average BLF (N) | Glide force, N 2-30 mm |
|---|---|---|---|
| WFI | 4 | 6.2 (0.2) | 2.1 (0.4) |
| Tween solution | 4 | 5.0 (0.2) | 1.6 (0.7) |

In Table 2 and Table 3, the numbers in brackets represent the standard deviations. Glide force gives the average forces for displacements between 2 mm and 30 mm. The average and standard deviation are computed for all data curves combined.

Thus, the stopper of the invention provided consistently low BLF values and also low glide force.

The same stoppers and glass injectors, i.e. stoppers having 1 deformable sealing element and stoppers having 2 deformable sealing elements, were also tested for Cylinder closure integrity (CCI). Specifically, the injectors were prefilled with blue dye solution prepared according to the guidelines in ASTM F 1929, and the tests were based on Pharmaceutical Package Integrity, Parenteral Drug Association's Technical Report No. 27, 1998. The injectors were laid on absorbent paper in a desiccator with the vacuum profile shown in Table 4 and Table 5.

TABLE 4

CCI test results for 1 ml injector,
1-deformable sealing element stopper

| Inspection after −25 mbar, 10 min | Inspection after −35 mbar, 10 min | Inspection after −100 mbar, 10 min |
|---|---|---|
| No leaking | No leaking | No leaking |

TABLE 5

CCI test results for 1 ml injector,
2-deformable sealing element stopper

| Inspection after −25 mbar, 10 min | Inspection after −35 mbar, 10 min | Inspection after −100 mbar, 10 min |
|---|---|---|
| No leaking | No leaking | No leaking |

No leaking indicates that the injection system can contain the dye during the vacuum challenges. Thus, the stoppers of the invention provide injectors complying with CCI requirements, also when the stopper has only a single deformable sealing element.

Example 2

Further experiments were conducted with the 1 ml injectors with either the one or two deformable sealing element stoppers to test the CCI and BLF over a period of time of up to 4 weeks. In contrast to Example 1, the injectors had cylinders of cyclic olefin polymer (COP). The injectors with the integrated needle were pre-filled with solutions of 0.10% surfactant (Tween80) in water and stored at 23° C., 50% relative humidity (RH) until testing began.

The area around the stopper was observed immediately after filling the injectors and after 1 hour, 1 week, 2 weeks and 4 weeks. No leakage was observed for any specimen and it was concluded that the injectors comply with CCI requirements.

For the measurements of BLF values, the injectors were tested with a stroke speed of 100 mm/min over 28 mm. The BLF values are shown in Table 6.

TABLE 6

| Specimen | BLF values over time | | | |
|---|---|---|---|---|
| | Immediately after filling | 1 week after filling | 2 weeks after filling | 4 weeks after filling |
| 1 deformable sealing element | 9.9 | 10.8 | 9.4 | 10.0 |
| 2 deformable sealing elements | 12.7 | 14.6 | 13.7 | 13.5 |

Thus, no significant development in BLF values was observed over a period of 4 weeks, which shows that the stopper of the invention is suited for use in a pre-filled injector. In all cases the BLF values were within an acceptable range.

REFERENCE NUMERALS

1001 Prior art stopper
1002 Piston body of prior art stopper
1003 Actuating end of prior art stopper
1004 Outlet end of prior art stopper
1005 Sealing element of prior art stopper
1006 Solid section of prior art stopper
1007 Tubular section of prior art stopper
1008 Internal helical thread of prior art stopper
1 Stopper of the invention
2 Stopper body
3 Actuating surface
4 Outlet surface
5 Deformable sealing element
51 Supporting sealing element
6 Cavity
7 Tubular section
71 Internal helical thread
72 Protrusion
81 Actuating stopper element
82 Outlet stopper element
83 Resilient frame
84 Compressible section
10 Piston rod
11 Engagement section
12 Ridge
13 Terminal site of piston rod
14 External helical thread
21 Injector
22 Cylinder
23 Inner wall of the cylinder

The invention claimed is:

1. An injector for delivery of a pharmaceutical composition, the injector comprising a cylinder having an inner wall, a piston rod, and a stopper having a stopper body with an actuating surface opposite an outlet surface, an axial length between the actuating surface and the outlet surface, and a transverse diameter, the stopper body having a tubular section having an access diameter, the stopper at an axial location from the actuating surface comprising a deformable sealing element made from a thermoplastic elastomer (TPE), which deformable sealing element surrounds the stopper body, has an outer diameter, which is larger than the transverse diameter, and a deformable sealing element axial extension in the range of 5% and 95% of the axial length of the stopper body, which deformable sealing element seals an annular gap between the stopper body and the inner wall of the cylinder, and the stopper comprising a cavity at the axial location of the deformable sealing element, the cavity comprising a compressible fluid and having a lateral extension larger than the access diameter and at least 50% of the outer diameter of the deformable sealing element and a cavity axial extension in the range of 5% to 50% of the axial length of the stopper body, and which cavity is formed at an interface between the stopper body and the piston rod and/or at an interface between the deformable sealing element and the piston rod.

2. The injector according to claim 1, wherein the cavity axial extension is in the range of 10% to 50% of the axial length of the stopper body.

3. The injector according to claim 1, wherein the cavity has a cylindrical, an ellipsoidal or a toroidal shape.

4. The injector according to claim 1, wherein the stopper body comprises an actuating stopper element and an outlet stopper element each comprising a deformable sealing element as defined in claim 1, which actuating stopper element and which outlet stopper element are linked together by a resilient frame, the outlet stopper element being located at a first axial location from the actuating surface, and the actuating stopper element being located at a second axial location from the actuating surface, the stopper having the cavity at the first axial location.

5. The injector according to claim 4, wherein the stopper comprises a second cavity at the second axial location.

6. The injector according to claim 4, wherein the resilient frame has a cylindrical shape.

7. The injector according to claim 1, wherein the deformable sealing element is an O-ring with a recess along the inner diameter of the O-ring so that upon mounting of the O-ring on the stopper body or the piston rod the cavity is formed between the O-ring and the stopper body or between the O-ring and the piston rod at the recess of the O-ring.

8. The injector according to claim 1, wherein the stopper body has a cylindrical shape and the deformable sealing element is comprised on a cylindrical structure for mounting on the stopper body or the piston rod, so that upon mounting of the cylindrical structure on the stopper body or the piston rod, the cavity is formed between the stopper body or the piston rod and the cylindrical structure.

9. The injector according to claim 1, wherein the deformable sealing element has or the stopper body and the deformable sealing element have a Shore A hardness in the range of 30 to 90.

10. The injector according to claim 1, wherein the stopper body is made from a TPE.

11. The injector according to claim 1, wherein the deformable sealing element is at a first axial location from the actuating surface and a cavity at the first axial location and wherein the stopper further comprises a second deformable sealing element at a second axial location from the actuating surface and a second cavity at the second axial location.

12. The injector according to claim 1, wherein the deformable sealing element is at a first axial location from the actuating surface and wherein the stopper further comprises a second deformable sealing element at a second axial location from the actuating surface and the cavity extends between the first axial location and the second axial location.

13. The injector according to claim 1, wherein the outer diameter of the deformable sealing element is in the range of 1.5% to 10% larger than the inner diameter of the cylinder before inserting the stopper into the cylinder.

14. The injector according to claim 1, wherein the deformable sealing element has a Shore A hardness in the range of 30 to 90, and wherein the injector does not comprise an external lubricant.

15. The injector according to claim 1, wherein the cylinder is made from glass.

16. The injector according to claim 1, wherein the cylinder has an inner diameter in the range of 2 mm to 12 mm.

17. The injector according to claim 1, wherein the cylinder is prefilled with a pharmaceutical composition.

18. The injector according to claim 1, wherein the deformable sealing element is convex and the deformable sealing element axial extension is in the range of 5% to 25% of the axial length of the stopper body.

19. The injector according to claim 1, wherein the stopper body has a diameter in the range of 50% to 90% of the outer diameter of the deformable sealing element.

20. The injector according to claim 1, wherein the deformable sealing element is convex and is further defined by an angle between the stopper body and the deformable sealing element, which angle is the range of 120° to 160°.

21. The injector according to claim 1, wherein the deformable sealing element is convex and an actuating contact angle facing the actuating surface of the stopper is formed between the inner wall of the cylinder and the deformable sealing element, which actuating contact angle is in the range of 5° to 60°.

22. The injector according to claim 1, wherein the deformable sealing element is convex and an outlet contact angle facing the outlet surface of the stopper is formed between the inner wall of the cylinder and the deformable sealing element, which outlet contact angle is in the range of 5° to 60°.

23. The injector according to claim 1, wherein the deformable sealing element is convex and an actuating contact angle facing the actuating surface of the stopper is formed between the inner wall of the cylinder and the deformable sealing element, and an outlet contact angle facing the outlet surface of the stopper is formed between the inner wall of the cylinder and the deformable sealing element, which actuating contact angle and outlet contact angle are independently in the range of 5° to 60°.

* * * * *